(12) United States Patent
Clamen et al.

(10) Patent No.: US 11,678,976 B2
(45) Date of Patent: *Jun. 20, 2023

(54) INJECTABLE PHYSIOLOGICALLY ADAPTIVE INTRAOCULAR LENSES (IOL'S)

(71) Applicant: Adaptilens, LLC

(72) Inventors: Liane Clamen, Chestnut Hill, MA (US); Paul Glazer, Chestnut Hill, MA (US); Michael T. Milbocker, Holliston, MA (US)

(73) Assignee: Adaptilens, LLC, Chestnut Hill, MA (US)

( * ) Notice: Subject to any disclaimer, the term of this patent is extended or adjusted under 35 U.S.C. 154(b) by 382 days.

This patent is subject to a terminal disclaimer.

(21) Appl. No.: 16/404,523

(22) Filed: May 6, 2019

(65) Prior Publication Data

US 2019/0321163 A1 Oct. 24, 2019

Related U.S. Application Data

(63) Continuation of application No. 13/096,729, filed on Apr. 28, 2011, now Pat. No. 10,278,810.

(Continued)

(51) Int. Cl.
*A61F 2/16* (2006.01)
*A61F 9/007* (2006.01)

(52) U.S. Cl.
CPC ............ *A61F 2/1635* (2013.01); *A61F 9/007* (2013.01)

(58) Field of Classification Search
CPC ...... A61F 2/1662; A61F 2/1678; A61F 2/167; A61F 2/1664; A61F 2/16; A61F 2/1635; A61F 9/007

See application file for complete search history.

(56) References Cited

U.S. PATENT DOCUMENTS

| 3,947,401 A | 3/1976 | Stamberger |
| 4,050,192 A | 9/1977 | Volk |

(Continued)

FOREIGN PATENT DOCUMENTS

| DE | 2518904 | * 4/1975 |
| JP | 04132547 | 5/1992 |

(Continued)

OTHER PUBLICATIONS

Assia El, Castaneda VE, Legler UFC, et al.: "Studies on Cataract Surgery and Intraocular Lenses at the Center for Intraocular Lens Research," Ophthalmol Clin. North Am 1991; 42(2):251-266.

(Continued)

*Primary Examiner* — Keri J Nelson
*Assistant Examiner* — Aren Patel
(74) *Attorney, Agent, or Firm* — Nutter, McClennen & Fish, LLP

(57) ABSTRACT

A device and method for forming an adaptive optic in the capsule of a human eye is disclosed, comprising a capsular interface enclosing an optically acceptable medium. The device establishes a physiologic range of optical power in response to a range of ciliary contractile states. The preferred bi-phasic medium of the device is comprised of a solid three dimensional polymeric network suspended in a liquid aqueous phase and bonded to a capsular interface. The polymeric network provides shape to the capsular interface, optical power, and a physiologic response to the suspensory ligament. The three dimensional network of the bi-phasic medium mimics the stacked fiber configuration and elasticity of a natural lens. An alternative embodiment utilizing a single phase medium is also disclosed with associated structural features provided in the capsular interface.

35 Claims, 16 Drawing Sheets

Related U.S. Application Data

(60) Provisional application No. 61/329,447, filed on Apr. 29, 2010.

(56) References Cited

U.S. PATENT DOCUMENTS

| | | | |
|---|---|---|---|
| 4,240,163 A | | 12/1980 | Galin |
| 4,297,446 A | * | 10/1981 | Lindner .................. C08K 5/544 |
| | | | 525/86 |
| 4,373,218 A | | 2/1983 | Schachar |
| 4,585,457 A | | 4/1986 | Kalb |
| 4,608,050 A | | 8/1986 | Wright et al. |
| 4,822,360 A | | 4/1989 | Deacon |
| 4,888,012 A | * | 12/1989 | Horn ..................... A61F 2/1613 |
| | | | 623/6.13 |
| 5,033,839 A | | 7/1991 | Bonbon et al. |
| 5,035,710 A | * | 7/1991 | Nakada ................. B29C 41/045 |
| | | | 623/6.13 |
| 5,041,134 A | | 8/1991 | O'Donnell |
| 5,073,021 A | | 12/1991 | Marron |
| 5,091,121 A | | 2/1992 | Nakada et al. |
| 5,106,180 A | | 4/1992 | Marie et al. |
| RE34,251 E | | 5/1993 | Achatz et al. |
| 5,213,579 A | | 5/1993 | Yamada et al. |
| 5,223,862 A | | 6/1993 | Dasher et al. |
| 5,278,258 A | | 1/1994 | Gerace et al. |
| 5,311,223 A | | 5/1994 | Vanderlaan |
| 5,391,590 A | | 2/1995 | Gerace et al. |
| 5,408,281 A | | 4/1995 | Zhang |
| 5,517,260 A | | 5/1996 | Glady et al. |
| 5,607,472 A | | 3/1997 | Thompson |
| 5,674,942 A | * | 10/1997 | Hill ..................... C08G 18/3228 |
| | | | 525/131 |
| 5,690,953 A | | 11/1997 | Molock et al. |
| 5,699,142 A | | 12/1997 | Lee et al. |
| 5,702,440 A | | 12/1997 | Portney |
| 5,725,575 A | * | 3/1998 | O'Donnell, Jr. ....... A61F 2/1629 |
| | | | 623/6.56 |
| 6,145,987 A | | 11/2000 | Baude et al. |
| 6,158,862 A | | 12/2000 | Patel et al. |
| 6,196,685 B1 | | 3/2001 | Roffman et al. |
| 6,361,561 B1 | | 3/2002 | Huo et al. |
| 6,520,637 B2 | | 2/2003 | Hodur et al. |
| 6,576,011 B2 | | 6/2003 | Portney |
| 6,589,550 B1 | | 7/2003 | Hodd et al. |
| 6,613,343 B2 | | 9/2003 | Dillingham et al. |
| 6,682,194 B2 | | 1/2004 | Ahsbahs et al. |
| 6,695,881 B2 | | 2/2004 | Peng et al. |
| 6,802,606 B2 | | 10/2004 | Roffman et al. |
| 6,858,305 B2 | | 2/2005 | Degand et al. |
| 7,004,585 B2 | | 2/2006 | Lindacher |
| 7,029,116 B2 | | 4/2006 | Roscini et al. |
| 7,060,095 B2 | | 6/2006 | Ho et al. |
| 7,073,906 B1 | | 7/2006 | Portney |
| 7,156,101 B2 | | 1/2007 | Terwee et al. |
| 7,160,324 B2 | | 1/2007 | Terwee |
| 7,182,780 B2 | | 2/2007 | Terwee et al. |
| 7,192,138 B2 | | 3/2007 | Lindacher et al. |
| 7,210,780 B1 | | 5/2007 | Bourdoncle et al. |
| 7,370,962 B2 | | 5/2008 | Roffman et al. |
| 7,377,641 B2 | | 5/2008 | Piers et al. |
| 7,404,638 B2 | | 7/2008 | Miller et al. |
| 7,427,134 B2 | | 9/2008 | Bourdoncle et al. |
| 7,441,894 B2 | | 10/2008 | Zhang et al. |
| 7,455,404 B2 | | 11/2008 | Bandhauer et al. |
| 7,559,949 B2 | | 7/2009 | Pinchuk |
| 7,621,949 B2 | | 11/2009 | Deacon et al. |
| 7,794,498 B2 | | 9/2010 | Pinchuk |
| 7,871,437 B2 | | 1/2011 | Hermans et al. |
| 10,278,810 B2 | | 5/2019 | Clamen et al. |
| 10,458,995 B2 | | 10/2019 | Moola |
| 10,982,266 B2 | | 4/2021 | Fouz et al. |
| 2003/0078657 A1 | | 4/2003 | Zadno-Azizi et al. |
| 2005/0070688 A1 | * | 3/2005 | Lewandowski ....... C08F 265/04 |
| | | | 528/425 |
| 2005/0113911 A1 | * | 5/2005 | Peyman ................... A61F 9/007 |
| | | | 623/6.11 |
| 2005/0131535 A1 | * | 6/2005 | Woods .................. A61F 2/1648 |
| | | | 623/6.37 |
| 2007/0213816 A1 | * | 9/2007 | Sarfarazi ................... A61F 2/14 |
| | | | 623/6.13 |
| 2007/0219633 A1 | * | 9/2007 | Gwon ..................... A61L 27/18 |
| | | | 623/6.56 |
| 2007/0269488 A1 | * | 11/2007 | Ravi ....................... A61L 27/50 |
| | | | 424/429 |
| 2008/0048350 A1 | * | 2/2008 | Chen ....................... C08L 83/14 |
| | | | 264/2.6 |
| 2008/0075756 A1 | * | 3/2008 | Gwon .................... A61K 9/1652 |
| | | | 424/429 |
| 2008/0095816 A1 | * | 4/2008 | Gordy ..................... C08L 83/04 |
| | | | 424/422 |
| 2009/0042936 A1 | * | 2/2009 | Ward ..................... A61K 45/06 |
| | | | 514/314 |
| 2009/0312836 A1 | | 12/2009 | Pinchuk et al. |
| 2010/0030332 A1 | | 2/2010 | Schedler |
| 2010/0047380 A1 | * | 2/2010 | Widman .......... B29D 11/00038 |
| | | | 425/174.4 |
| 2010/0211170 A1 | * | 8/2010 | Liao .......................... A61F 2/16 |
| | | | 623/6.34 |
| 2011/0035001 A1 | * | 2/2011 | Woods .................. A61F 2/1648 |
| | | | 623/6.37 |
| 2011/0118834 A1 | | 5/2011 | Lo et al. |
| 2011/0190876 A1 | | 8/2011 | Zhao |
| 2012/0303118 A1 | | 11/2012 | DeBoer et al. |
| 2014/0111765 A1 | | 4/2014 | DeBoer et al. |
| 2015/0366660 A1 | | 12/2015 | Fernandez Martinez et al. |
| 2016/0184222 A1 | | 6/2016 | Gaillard et al. |
| 2017/0274221 A1 | | 9/2017 | Barrau et al. |
| 2018/0001581 A1 | | 1/2018 | Patel et al. |
| 2018/0085065 A1 | | 3/2018 | Haffner et al. |
| 2018/0164608 A1 | | 6/2018 | Schmeder et al. |
| 2018/0271642 A1 | | 9/2018 | Wortz et al. |
| 2021/0187166 A1 | | 6/2021 | Banquy et al. |

FOREIGN PATENT DOCUMENTS

| | | |
|---|---|---|
| WO | WO-200022459 A1 | 4/2000 |
| WO | WO-200022460 A1 | 4/2000 |
| WO | WO-200176651 A1 | 10/2001 |
| WO | 2011057286 A1 | 5/2011 |
| WO | 2014169073 A1 | 10/2014 |
| WO | 2015081088 A1 | 6/2015 |
| WO | 2017015132 A1 | 1/2017 |
| WO | 2017181274 A1 | 10/2017 |
| WO | 2018106738 A1 | 6/2018 |
| WO | 2021141662 A1 | 7/2021 |
| WO | 2021146553 A1 | 7/2021 |

OTHER PUBLICATIONS

International Search Report and Written Opinion for Application No. PCT/US2020/052316 dated Dec. 10, 2020, 12 pages.

* cited by examiner

INJECTABLE PHYSIOLOGICALLY ADAPTIVE INTRAOCULAR LENSES (IOL'S)

CROSS-REFERENCE TO RELATED APPLICATIONS

This application is a continuation of U.S. patent application Ser. No. 13/096,729 filed Apr. 28, 2011, which claims the benefit of priority to U.S. Provisional Application Ser. No. 61/329,447, filed Apr. 29, 2010. The entire contents of each of the foregoing applications are incorporated by reference herein in their entirety.

BACKGROUND OF THE INVENTION

1. Field of the Invention

The present invention relates to treating eyes, and more particularly to devices and methods for forming an adaptive optic in the capsule of a human eye.

2. Description of Related Art

Referring to FIGS. 1A and 1B, the zonule of Zinn (Zinn's membrane, ciliary zonule) is a ring of fibrous strands 52 connecting the ciliary body with the crystalline lens 54 of the eye. The zonule of Zinn is split into two layers: a thin layer which lines the hyaloid fossa and a thicker layer which is a collection of zonular fibers. Collectively, the fibers are known as the suspensory ligament of the lens. The action of the suspensory ligament is to place tension on the capsule 56 (shown in partial section view) of the lens 54 to keep it centered on the eye. While the suspensory ligament accommodates the optics of the eye by changing the magnitude of tension on the capsule, the capsule is nevertheless in tension through all accommodative states of a normal eye. Correspondingly, when an intraocular lens (IOL) is placed in the eye it is not bonded to the capsule and hence is not in tension. Currently the only means for centering an IOL implanted within the capsule is to provide structure which creates forces between the IOL and the capsule to center the IOL. This is accomplished with haptics, small loop shaped springs on the equator of the lens, which apply a compressive force along the equator of the lens. The net effect is to increase the tension placed on the capsule at the equator, rendering ineffective any changes in the ciliary muscle fibers which otherwise would change the shape of a material lens to provide accommodation and alter the power of the lens. In the normal lens, as the ciliary muscles contract (like a sphincter) the zonules relax and the lens becomes rounder to provide accommodation and variable power. Today's flat IOLs need haptics to keep the IOL in place. The haptics do not maintain the natural shape of the capsular bag. The zonular fibers surrounding the capsule are thus relaxed beyond the normal range of contraction of the ciliary muscle. Thus the ciliary muscle cannot relax the zonular fibers more, and the capsular bag remains in a position of over accommodation. Thus, physiological accommodation is not possible with any type of thin and flat IOL. It is a further object of the present invention to provide an IOL with an approximately ellipsoidal profile.

This release of tension of the zonular fibers causes the lens to become more spherical, thereby increasing the power of the lens to focus on near objects.

Referring again to FIGS. 1A and 1B, to understand the sensitivity of the accommodative function, it is important to recognize there are both radial 62 and anterior-posterior (AP) zonular fibers (64 and 66). According to the Schachar hypothesis when the ciliary muscle contracts, AP zonular tension is increased (the angle between 64 and 66 increases) while radial zonular fiber tension decreases. The increase in AP zonular tension occurs peri-circumferentially causing the central surfaces of the crystalline lens 54 to steepen, the central thickness of the lens to increase (increasing the anterior-posterior diameter), and the peripheral surfaces of the lens to flatten. While the tension on AP zonules is increased during accommodation, the radial zonules are simultaneously relaxing.

As a consequence of the changes in lens shape during human in vivo accommodation, the central optical power of the lens increases and spherical aberration of the lens shifts in the negative direction. Because of the increased AP zonular tension on the lens during accommodation, the surface tension of the lens capsule is increased despite the reduction in radial tension and the lens remains stable and unaffected by gravity. To be more specific, the surface tension is actually the interaction between the AP zonular tension and the anterior-posterior connectivity provided by the fibular structure 70 of the lens 54. This is an important feature striking a compromise between low modulus and resistance to distortion by gravity. The same shape changes that occur to the crystalline lens during accommodation are observed when circumferential tension is applied to any encapsulated biconvex object that encloses a minimally compressible material (volume change less than approximately 3%) and has an elliptical profile at the equator of the lens with an aspect ratio≤0.6 (minor axis/major axis ratio). The fibular structure of the lens is likely responsible for maintaining the aspect ratio below 0.6 of the elliptical profile. Circumferential tension is very efficient when applied to biconvex objects that have a profile with an aspect ratio≤0.6. Minimal circumferential tension tends to flatten the equator of the lens, slightly increasing the lateral equatorial diameter and causing a large increase in central curvature resulting in a more spherical-shaped lens. Vertebrates that have lenses with aspect ratios≤0.6 have high amplitudes of accommodation; e.g., primates and falcons, while those vertebrates with lenticular aspect ratios>0.6 have low amplitudes of accommodation; e.g. owls and antelopes.

The decline in the amplitude of accommodation eventually results in the clinical manifestation of presbyopia. It has been widely suggested that the age-related decline in accommodation that leads to presbyopia occurs as a consequence of sclerosis (hardening) of the lens. However, the lens does not become sclerotic until after 40 years of age. In fact, the greatest decline in the amplitude of accommodation occurs during childhood, prior to the time that any change in hardness of the lens has been found. The decline in accommodative amplitude, rapid in childhood and slow thereafter, follows a logarithmic pattern that is similar to that of the increase in the equatorial diameter of the lens, which is the most likely basis for the accommodative loss. As the equatorial diameter of the lens continuously increases over life, baseline ciliary tension simultaneously declines. This results in a reduction in baseline ciliary muscle length that is associated with both lens growth and increasing age. Since the ciliary muscle, like all muscles, has a length-tension relationship, the maximum force the ciliary muscle can apply decreases, as its length shortens with increasing age. This is the etiology of the age-related decline in accommodative amplitude that results in presbyopia. Any implant that increases radial compression internal to the capsule (directed outward), increases the equatorial lens diameter and decreases the amplitude of accommodation.

Thus, an IOL which is responsive to the natural accommodative mechanism of the human eye preferably possesses the following properties:
1. Does not apply a radial force directed outwards near the equatorial plane of the capsule, so as not to work against accommodation.
2. Possesses a centering mechanism largely based on volume of the IOL relative to the volume of the natural capsule
3. Is resistant to gravitationally induced asymmetry, yet is highly compliant
4. Possesses an internal structure that tends to stabilize the shape of the IOL in an ellipse with an aspect ratio approximately <0.6
5. The surface of the IOL follows, without relative motion, changes in shape of the natural capsule
6. Possesses approximately the same modulus or less than the capsule
7. Possesses a fixed index of refraction discontinuity relative to the capsule
8. Possesses approximately the same water content as lens matter
9. Is naturally buoyant (same specific gravity as surrounding tissue)
10. Provides a means to adjust the set point dioptric power during implantation
11. Provides an accommodative dioptric range of 15 Diopters
12. Provides capsule filling lens volume
13. Requires minimal surgical disruption by being formed at the implantation site
14. Has a minimized lens thickness Requirements 12 and 14 appear to be contradictory, and it is this contradiction that will be addressed presently. The focal length of an implanted IOL can be calculated from $$\phi = \frac{1}{f} = (n-1.33)\left[\frac{1}{R_1} - \frac{1}{R_2} + \frac{(n-1.33)d}{nR_1R_2}\right]$$

Where f is the focal length of the lens,
n is the refractive index of the lens material,
$R_1$ is the radius of curvature of the lens surface closest to the light source,
$R_2$ is the radius of curvature of the lens surface farthest from the light source,
d is the thickness of the lens (the distance along the lens axis between the two surface vertices).
$\Phi$ is the optical power in diopters if R is in meters.

The signs of the lens' radii of curvature indicate whether the corresponding surfaces are convex or concave. The sign convention used to represent this varies, but here if $R_1$ is positive the first surface is convex, and if $R_1$ is negative the surface is concave. The signs are reversed for the back surface of the lens: if $R_2$ is positive the surface is concave, and if $R_2$ is negative the surface is convex. If either radius is infinite, the corresponding surface is flat. With this convention the signs are determined by the shapes of the lens surfaces, and are independent of the direction in which light travels through the lens.

Making the simplifying assumption R1=−R2, $$\phi = \frac{1}{f} = (n-1.33)\left[\frac{2}{R_1} - \frac{(n-1.33)d}{nR_1^2}\right]$$

Then the second term $$\frac{(n-1.33)d}{2nR_1^2}$$

subtracts from the first, reducing the power of the optical system. Decreasing the radius of curvature, making the lens rounder, increases the second term much faster than the first term. The zero power condition, $\phi=0$, occurs when $$\frac{2}{R_1} - \frac{(n-1.33)d}{nR_1^2} = 0$$

Or $$\frac{2nR_1}{(n-1.33)} = d$$

When the lens is a perfect sphere, R is about 4 mm and $$\frac{2n}{(n-1.33)}$$

is approximately 8, so d is approximately 8R. Accordingly, it is very important that the IOL not be compressed equatorially. This is perhaps the reason why the natural lens is always in tension with the suspensory ligament. Placing an equatorial ring inside a compliant IOL which is not suspended within the capsule is not preferred because it would almost certainly degrade accommodation range during ciliary contraction or become de-centered during ciliary dilation. An IOL which places an outward radial force on the capsule, a lens configured like the Crystalens, would be predisposed to one or both of these limitations.

It is worth noting that d is 0 if the equator of the lens is not flattened at any point during accommodation (refer back to the definition of d). Suspension readily accomplishes this criterion for any volume of lens capable of fitting within the capsule, whereas a passively inserted bag-like IOL would suffer significant optical power loss if the equatorial perimeter of the IOL were to sag away from the equator of the capsule, or otherwise not be actively suspended by the capsule. Conversely, any inserted ring or bag thickening around the equator to keep the lens in contact with the capsule would resist accommodation, or worse cause the equator to fold under accommodation. One solution is to glue or otherwise attach the bag-lens to the equator of the capsule so that during all phases of accommodation the bag is in tension. This would require the bag to be highly elastic.

It is instructive to consider the specific composition of the natural lens and capsule. Referring to FIG. 1C, the lens capsule 75 is a smooth, transparent basement membrane that completely surrounds the lens. The capsule is elastic and is composed of collagen. It is synthesized by the lens epithelium and its main components are Type IV collagen and sulfated glycosaminoglycans (GAGs). The capsule is very elastic and so causes the lens to assume a more globular shape when not under the tension of the zonular fibers, which connect the lens capsule to the ciliary body. The capsule varies from 2-28 micrometers in thickness, being thickest near the equator 77 and thinnest near the anterior 79 and posterior 80 poles.

Referring now to FIGS. 1A and 1B, the lens fibers 70 form the bulk of the lens 54. They are long, thin, transparent cells, firmly packed, with diameters typically between 4-7 micrometers and lengths of up to 12 mm long. The lens fibers stretch lengthwise from the posterior to the anterior poles and, when cut horizontally, are arranged in concentric layers 80 rather like the layers of an onion. If cut along the equator, it appears as a honeycomb 70. The middle of the fibers is at the equator 60. The middle of each fiber lies in the equatorial plane. These tightly packed layers of lens fibers are referred to as laminae 80. The lens fibers are linked together via gap junctions and interdigitations of the cells that resemble "ball and socket" forms. It is this later feature that enables the fibers to be stretched in the axial direction without sagging in the equatorial plane. Thus, in order to enable a bag-like IOL one prefers the IOL to be filled with a series of elastic rods preferring an extended length, the extended rod lengths chosen such that they are shaped to the radius of curvature achieved at the high power extreme of the accommodative optical power spectrum while each rod in all accommodative states experiences approximately the same magnitude of tension-compression. To achieve this each rod needs to be articulated laterally with its neighboring rods. The rods must be suspended in a fluid, incompressible medium. And the rod ends must be bonded to either the natural capsule or a synthetic tightly fitting bag, such that the shape of the bag is substantially a function of the axial and lateral spring constants of the rods and their lateral pivoting connector. The lateral pivoting connection must be both elastic and pivoting in order to provide for equatorial diameter change that does not overly constrain lens axial lengthening.

Heretofore, a number of patents and publications have disclosed IOL devices and other optical implant devices, the relevant portions of which may be briefly summarized as follows.

U.S. Pat. Nos. 5,213,579 and 5,091,121 describe an intraocular lens including a balloon member formed of an elastomers and adapted to be inserted into a capsular bag of an eye, an optically transparent fluid which is injected into the balloon member so that the balloon member expands and fills the capsular bag, and a tube provided on the balloon member and having a bore through which the optically transparent fluid is injected into the balloon member. The bore of the tube is filled with and closed by a gel filler. The fluid serving as a lens medium is injected into the balloon member through the tube, with the gel filler inhibiting leakage of the fluid from the balloon member.

U.S. Pat. No. 5,391,590 discloses an injectable intraocular lenses. In one embodiment, such injectable compositions comprise polymer mixtures derived from the polymerization, for example, cross-linking, of curable components in precursor mixtures. These precursor mixtures comprise curable component comprising: (A) an unsaturation functional (vinyl group-containing) polyorganosiloxane component, (B) an organosilicon component including silicon-bonded hydride groups which react with the unsaturation functional groups included in (A) during the polymerization, and (C) an effective amount of a platinum group metal-containing catalyst component; and a polymer component which is substantially non-functional.

U.S. Pat. No. 6,613,343 relates to pre-polymerized compositions comprising polysiloxanes suitable for the preparation of accommodating intraocular lenses, having a specific gravity of greater than about 1.0, a refractive index suitable for restoring the refractive power of the natural crystalline lens and a viscosity suitable for injection through a standard cannula.

U.S. Pat. No. 6,361,561 describes polysiloxanes suitable for the preparation of intraocular lenses by a crosslinking reaction, having a specific gravity of greater than about 1.0, a refractive index suitable for restoring the refractive power of the natural crystalline lens and a viscosity suitable for injection through a standard cannula.

U.S. Pat. No. 3,947,401 discloses an intraocular lens assembly for increased depth of focus and has a frame configured to vault posteriorly in an eye and an optic attached thereto. Pressure from ciliary muscle contraction moves the optic anteriorly to focus the eye for near vision. U.S. Pat. No. 3,947,401 discloses a bulk polymerized, water insoluble but water swellable polymer of monomers comprising water soluble monoester of acrylic or methacrylic acid with a polyhydric alcohol; and glycidyl methacrylate, and/or glycidyl acrylate, and/or glycidyl crotonate. The polymer may be swelled in aqueous solution to provide a transparent hydrogel having excellent physical properties, and suitable in an ophthalmic lens.

U.S. Pat. No. 4,050,192 discloses a multifocal ophthalmic lens of homogeneous transparent optical material and method and apparatus for forming same, useful for the correction of the refractive error and the accommodative insufficiency or absence of accommodation in presbyopia and in aphakia, the lens characterized by having a unique variable front surface and a coacting spherical or toric back surface, said variable front surface characterized by being geometrically and optically regular and continuous and having a pair of intersecting orthogonal principal planes.

U.S. Pat. No. 5,073,021 discloses a dual focal length ophthalmic lens formed from a birefringent material with its fast and slow axes perpendicular to the user's visual axis. The dual focal property arises due to the differing indices of refraction of the birefringent material for light polarized parallel to the fast and slow axes. Light emanating from far objects having one polarization and light emanating from near objects having the opposite polarization are both focused onto the user's retina. Depending upon which object is being viewed, an in-focus and a blurred image appear simultaneously on the user's retina. The ability of the user's eye/brain system to distinguish between the two images provides bifocal action from a single lens.

U.S. Pat. No. 5,223,862 discloses an ophthalmic lens embodying an organic plastic lens member having a refractive index of at least 1.56 and being the cured product of a monomeric formulation. The formulation contains a resin monomer base, a curing agent selected from aromatic anhydrides, aromatic diamines, thioamides and thioamines, and a refractive index enhancing additive selected from alkyl or aromatic diols or thiols and transition metal alkoxides. The organic plastic lens member may be an integral, monofocal lens, or a segment embedded in a cavity in the front, convex surface of an organic plastic, major lens member having a lesser refractive index. The latter may have a thin, inorganic glass lens member adhered to its front, convex surface to produce a glass-plastic, laminated, multifocal lens structure.

U.S. Pat. No. 5,408,281 discloses a multifocal ophthalmic lens with a spiral-like pattern on its surface in an area overlying the cornea of a wearer of the lens. The spiral-like pattern is capable of providing a plurality of different dioptric powers.

U.S. Pat. No. 5,690,953 discloses a soft hydrogel contact lens derived from a crosslinked polymer made by reacting a hydrophilic monomer with a cross linking amount of a polyfunctional compound containing a saccharide residue.

U.S. Pat. No. 5,702,440 discloses a multifocal ophthalmic lens having outer annular zones with vision correction powers less than a far vision correction power of the patient, is disclosed. These additional annular zones come into play, when the pupil size increases under dim lighting conditions, to thereby compensate for the near-vision powered annular zones. The net effect of the additional near vision annular zones and the additional annular zones having power less than the far vision correction power is to shift the best quality image from in front of the retina to an area on the retina of the eye U.S. Pat. No. 6,158,862 discloses a multifocal ophthalmic lens having a dye or dyes that block the transmission of near UV and/or blue light.

U.S. Pat. No. 6,520,637 discloses an ophthalmic lens with a posterior surface and an anterior surface having a spherical central optical correction zone, an aspheric intermediate zone, and a peripheral zone.

U.S. Pat. No. 6,682,194 discloses a progressive multifocal ophthalmic lens having a far vision region, an intermediate vision region and a near vision region, a main meridian of progression passing through said three regions, and a power addition equal to a difference in mean sphere between a near vision region control point and a far vision region control point is provided.

U.S. Pat. No. 6,858,305 discloses an organic glass ophthalmic lens having an impact-resistant primer layer based on polyurethane latex and its manufacturing process.

U.S. Pat. No. 7,029,116 discloses an ophthalmic lens for nearsightedness, manufactured as a finished or semi-finished lens, lighter and thinner at the edges, with a wide visual field and cosmetically attractive, featuring a spherical centre and an aspherical periphery, both asymmetrical to the lens optical centre and varying in width.

U.S. Pat. No. 7,192,138 discloses an ophthalmic lens with an optical zone with a first corrective power range in a first region and a second corrective power range in an annular region surrounding the first optical zone.

U.S. Pat. No. 7,370,962 discloses an invention with a multifocal ophthalmic lens that both corrects for the wearer's refractive prescription and takes into account pupil size of a specific individual or of a population of individuals.

U.S. Pat. No. 7,404,638 discloses a method and apparatus for increasing the depth of focus of the human eye is comprised of a lens body, an optic in the lens body configured to produce light interference, and a pinhole-like optical aperture substantially in the center of the optic.

U.S. Pat. No. 7,441,894 discloses a trifocal ophthalmic lens that includes an optic having at least one optical surface, and a plurality of diffractive zones that are disposed on a portion of that surface about an optical axis of the optic.

U.S. Pat. No. 7,559,949 discloses an injectable intraocular lens formed in situ.

U.S. Pat. No. RE34,251 discloses a multifocal, especially bifocal, intraocular, artificial ophthalmic lens of transparent material, whose optical lens portion is divided into near range and far range zones and, each of which is disposed on the optical lens portion with approximately equal surface proportions and symmetrically with the lens axis.

U.S. Pat. No. 5,033,839 discloses a unifocal ophthalmic lens with part-spherical concave and convex surfaces.

U.S. Pat. No. 5,106,180 discloses an ophthalmic lens with front and rear optical surfaces, a central optical axis substantially perpendicular to the lens and comprises a plurality of concentric, contiguous circular refractive bands provided on at least one of the front and rear optical surfaces.

U.S. Pat. No. 5,311,223 discloses an ophthalmic lens with a polymer composition composed of the reaction product of a hydrophilic monomer and an acyclic monomer is disclosed.

U.S. Pat. No. 5,517,260 discloses an ophthalmic lens including a first zone located in a central portion of the ophthalmic lens such that a central axis intersects the center of the first zone. The first zone having a spherical posterior surface for correcting distance vision. The ophthalmic lens further includes a second zone, positioned about the periphery of the first zone, and having a posterior surface of revolution defined by rotating a portion of a spiral curve about a central axis of the ophthalmic lens.

U.S. Pat. No. 5,699,142 discloses a multifocal ophthalmic lens including an apodization zone with echelettes having a smoothly reduced step height to shift the energy balance from the near image to the distant image and thus reduce the glare perceived when viewing a discrete, distant light source.

U.S. Pat. No. 6,145,987 discloses a multifocal ophthalmic lens with spherical aberration varying with the addition and the ametropia.

U.S. Pat. No. 6,196,685 discloses a method for fitting and designing an ophthalmic lens for a presbyope that yields improved visual acuity in general, and takes into account individual fitting characteristics.

U.S. Pat. No. 6,576,011 discloses a multifocal ophthalmic lens, having outer annular zones with vision correction powers less than a far vision correction power of the patient, is disclosed. These additional annular zones come into play, when the pupil size increases under dim lighting conditions.

U.S. Pat. No. 6,802,606 discloses a progressive multifocal ophthalmic lens pair in which the dominant eye lens incorporates more distance vision correction than does the lens for the non-dominant eye.

U.S. Pat. No. 7,004,585 discloses a lens with an anterior surface and an opposite posterior surface, wherein the anterior surface includes a vertical meridian, a horizontal meridian, and a central optical zone having at least a first optical zone for primary gaze, a second optical zone for down-gaze and an optical blending zone between the first and second optical zones.

U.S. Pat. No. 7,073,906 discloses a multifocal ophthalmic lens with a lens element having anterior and posterior surfaces with a central aspherical refractive zone disposed on one of the anterior and posterior surfaces; and a diffractive bifocal zone disposed outside of the aspherical refractive zone.

U.S. Pat. No. 7,210,780 discloses a method for determination by optimization of an ophthalmic lens for a wearer for whom a power addition has been prescribed.

U.S. Pat. No. 7,377,641 discloses a multifocal ophthalmic lens with one base focus and at least one additional focus, capable of reducing aberrations of the eye for at least one of the foci after its implantation, comprising the steps of: (i) characterizing at least one corneal surface as a mathematical model; (ii) calculating the resulting aberrations of said corneal surface(s) by employing said mathematical model; (iii) modeling the multifocal ophthalmic lens such that a wave front arriving from an optical system comprising said lens and said at least one corneal surface obtains reduced aberrations for at least one of the foci.

U.S. Pat. No. 7,427,134 discloses a multifocal ophthalmic lens with a complex surface having a prism reference point, a fitting cross, a progression meridian having a power addition greater than or equal to 1.5 diopters.

U.S. Pat. No. 7,455,404 discloses an ophthalmic lens for providing a plurality of foci has an optic comprising an anterior surface, a posterior surface, and an optical axis. The optic has a first region and a second region. The first region has a refractive optical power and comprises a multifocal phase plate for forming a first focus and a second focus.

Most IOLs in use today are composed of a thin optic (usually less than 1.0 mm at the thickest dimension) attached to haptics which center the IOL and keep it in place. Haptics apply radial or equatorial pressure to the suspensory ligament, compromising accommodation. It is an object of the present invention to provide an IOL that does not require haptics to stay centered in the eye capsule.

The current thin optic of IOL's available prior to the present application replace nature's 4.0-5.0 mm thick crystalline lens with a much flatter lens (on the order of 1 mm in anterior-posterior thickness). The flatness of the lens results in increases in the depth and volume of both the anterior chamber and the vitreous cavity. The vitreous body consequently has more space in which to move, and this instability has been associated with an increased incidence of retinal breaks and detachment. This problem is more significant if posterior vitreous detachment has not yet occurred.

Multifocal lenses do provide functional "pseudo accommodation." However, this optical goal of multifocality is achieved at the expense of other important visual qualities: multifocal lenses create increased glare, and decreased contrast sensitivity and color discrimination. It is further an object of the present disclosure to provide an IOL having improved contrast sensitivity and color discrimination without undesirable glare.

Currently, the Crystalens IOL (Eyeonics, Inc., Aliso Viejo, Calif.) is the only FDA-approved accommodative IOL. This lens is similar to a traditional IOL in that it has an optic and haptics. However, unlike the traditional flat IOLs, the Crystalens has a movable haptic-optic junction that functions like a hinge and theoretically produces accommodation. Like traditional multipiece IOLs, of course, the Crystalens induces posterior capsular opacification, which requires post-operative Nd:YAG capsultomoties. This laser procedure creates an additional expense and potential complications, such as an increased risk of retinal detachments. Finally, such destruction of the posterior capsule may hinder the accommodative ability of this IOL. It is further an object of the present invention to provide an IOL which does not damage adjacent tissue.

Such conventional methods and systems have generally been considered satisfactory for their intended purpose. However, there is a need for a crystalline lens replacement with a close functional approximation of the healthy lens: a lens with varying dioptric power that is enclosed within the natural capsule. In this way, the ciliary muscles remain effective. There is a need for an IOL responsive to the ciliary muscle ring, such that when the IOL is implanted the zonular fibers surrounding the lens are not placed in a permanently relaxed state, allowing the lens to become more spherical than it would otherwise. The present invention provides a solution for these problems.

It is further an object of the present invention to replace the current technology of IOLs that imitate a presbyopic lens with a new IOL that imitates nature's accommodative lens. It is yet another object of the present invention to provide an injectable IOL to allow for a minimally-invasive limbal incision. Studies have shown that pressure exerted on the capsular bag reduces epithelial cell proliferation or migration at the area of contact. (Assia E I, Castaneda V E, Legler U F C, et al. Studies on cataract surgery and intraocular lenses at the Center for Intraocular Lens Research. Ophthalmol Clin North Am 1991; 4(2):251-266.) It is yet another object of the present invention to provide an optic that will not rub against the posterior capsular bag and will not create opacification of the posterior lens capsule.

SUMMARY OF THE INVENTION

The subject invention is directed to a new and useful intraocular lens for assisting the function of a human eye disposed within a body. The intraocular lens includes an outer wall or bag which may be filled. The bag may be compressed, such as by rolling, to a minimum diameter suitable for insertion into an incision at the limbus of the eye (where the cornea meets the sclera) and through a capsulorrhexis, a circular central opening in the anterior capsule of the crystalline lens. Optimally, the bag may be inflated within a space made within the capsule formed by removing the lens fibers, and oriented such that the equator of the bag is adjacent the capsular equator. The bag may then be deflated in preparation of receiving a liquid filling optical medium which cures to a substantially solid state after entering the bag. Preferably, the filling material cures to form cross links between the anterior and posterior surfaces of the bag. This cross-linking provides internal structure to the lens.

There is further provided an IOL for assisting the accommodative function of an eye disposed within a body having an outer wall, the IOL including an ellipsoid of revolution shape having an exterior wall, an interior wall, an anterior pole, and a posterior pole; an equatorial margin with an outer surface and an inner surface, an inner medium joined to said interior wall so as to form an incompressible volume between said anterior pole and posterior pole; and the inner medium preferably comprised of a fluid phase and a solid phase, the solid phase applying a variety of restorative forces on at least a portion of the outer wall of the IOL. The optional solid phase and liquid phase combination may facilitate accommodation. Thus, if the filling material were 100% in the liquid phase, the amount of force required to alter and maintain the shape of the lens is likely to be higher than if a portion of the lens is solid and only a portion of the filling is in the liquid phase and needs to be moved or reshaped to achieve accommodation. Thus, if a portion of the filling is solid, either as a result of being preformed prior to insertion or because that portion of the filling material solidifies in situ, and is surrounded by a liquid or gel material which is more pliable than the solid phase, as the muscles adjust to change the shape of the lens the solid portion will remain intact while only the liquid or gel portion is deformed around the solid portion to adjust lens power.

There is further provided a method for assisting the function of a human eye disposed within a body, including an outer wall and liquid filling medium, the method including a focal length assessment means; an IOL insertion means; an IOL inflation means such that when the liquid filling medium is delivered to the IOL disposed within the capsule of a human eye the focal length assessment means provides for real-time assessment of the focal length of the IOL relative to the retina of the eye during filling. This method may be particularly useful where the lens is formed in situ in multiple "pours" that is, injecting a portion of the filling material, assessing the lens, and adding additional filling material in one or more additional injections until the desired lens characteristics are achieved.

There is further provided a method for assisting the function of a human eye disposed within a body, including an outer wall, the method including the steps of partially filling an inflatable IOL lens disposed within the capsule of a human eye until the equatorial circumference of the IOL is in juxtaposition with the equatorial circumference of the capsule; allowing the filling medium to cure to form a first half defining an equatorial plane within the IOL, introducing additional filling medium until the IOL is inflated to a desired curvature during which time a focal length measurement means can be employed to determine the proper final curvature of the IOL; allowing the additional filling medium to cure while the patient is in a recumbent position, and disconnecting the filling means from said IOL.

The IOL described herein is advantageous because compared to other devices, it utilizes natural accommodation to precisely vary the optical power of the eye without damaging the tissue thereof, or the circulating aqueous materials. In a preferred embodiment the IOL uses at least one in situ curing medium to ensure the IOL-eye system re-establishes the accommodative mechanism so that the optical system of the patient can respond to changes in spatial images and illumination; permitting the lens to be installed by a simple procedure that can be quickly performed. In addition, the IOL localizes in the natural capsule so as to minimize de-centering and accommodation loss; providing functional performance similar to a natural eye; and allowing volumetric accommodation so that the ciliary muscle can control accommodation of the IOL. As a result, a greater variety of patients with lens disease can be provided with natural, responsive acuity, under a greater variety of circumstances, including but not limited to, enhanced capacity for accommodation, reduced glare, and extended or even permanent functionality because it utilizes a novel combination of solid and liquid phases to enhance the optical performance of the eye and establish normal visual experience.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figure 1A:
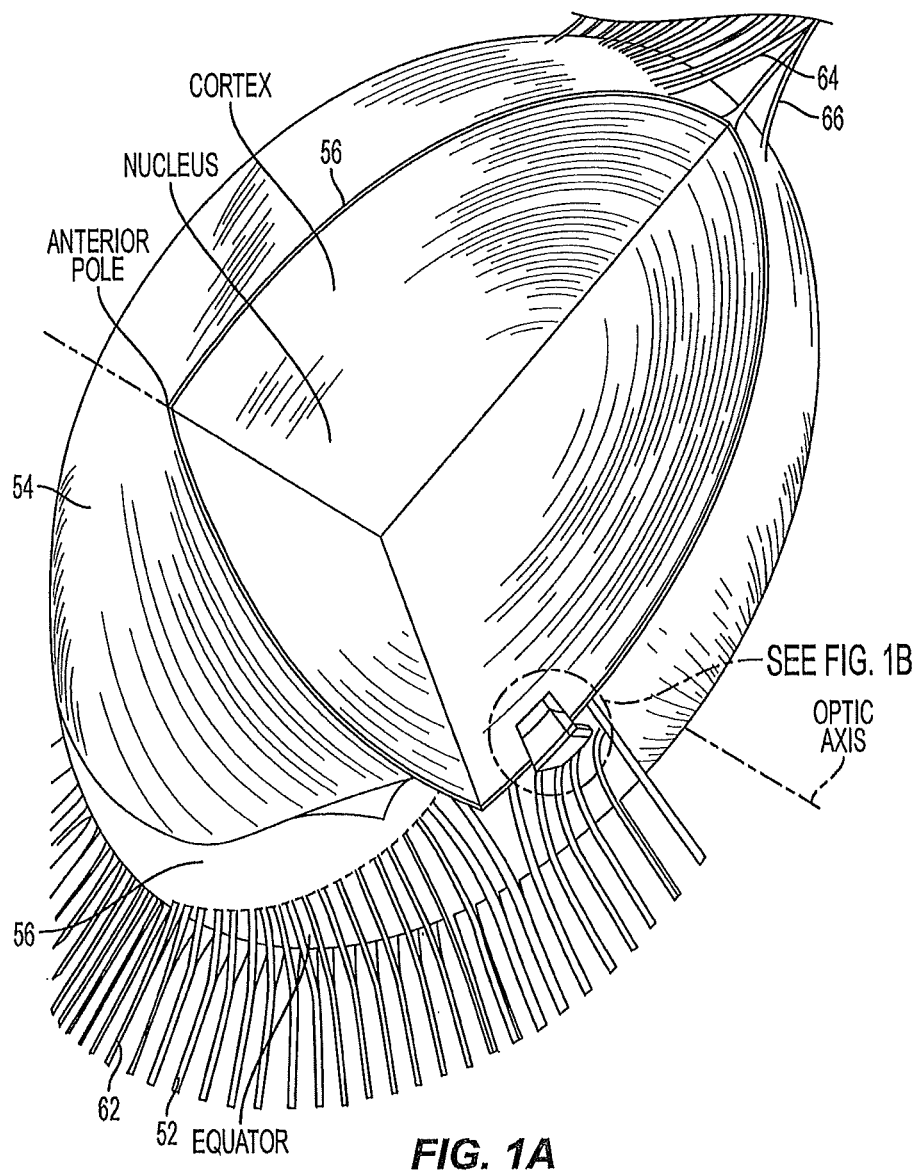
FIG. 1A is a cut-away perspective view of the lens structure of the human eye.
Figure 1B:
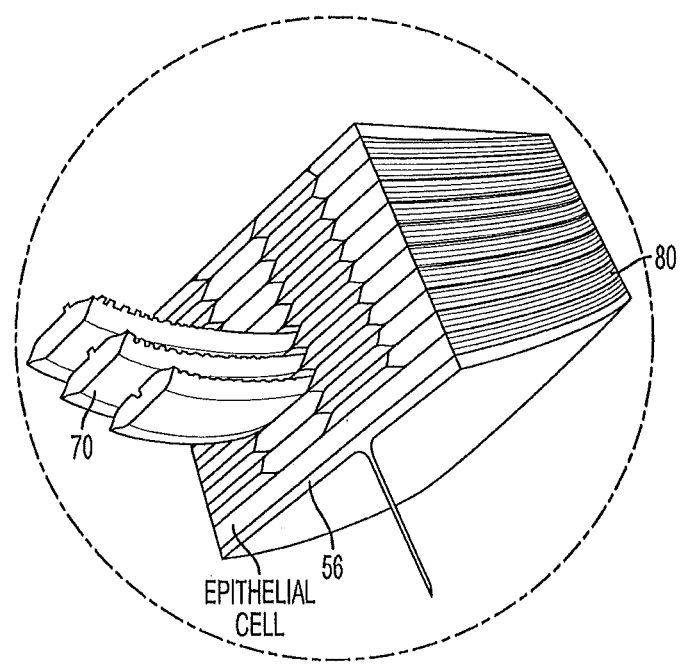
FIG. 1B is a cross-sectional perspective view of a portion of the human eye of FIG. 1A, showing the capsule, epithelial cell, and fiber layers.
Figure 1C:
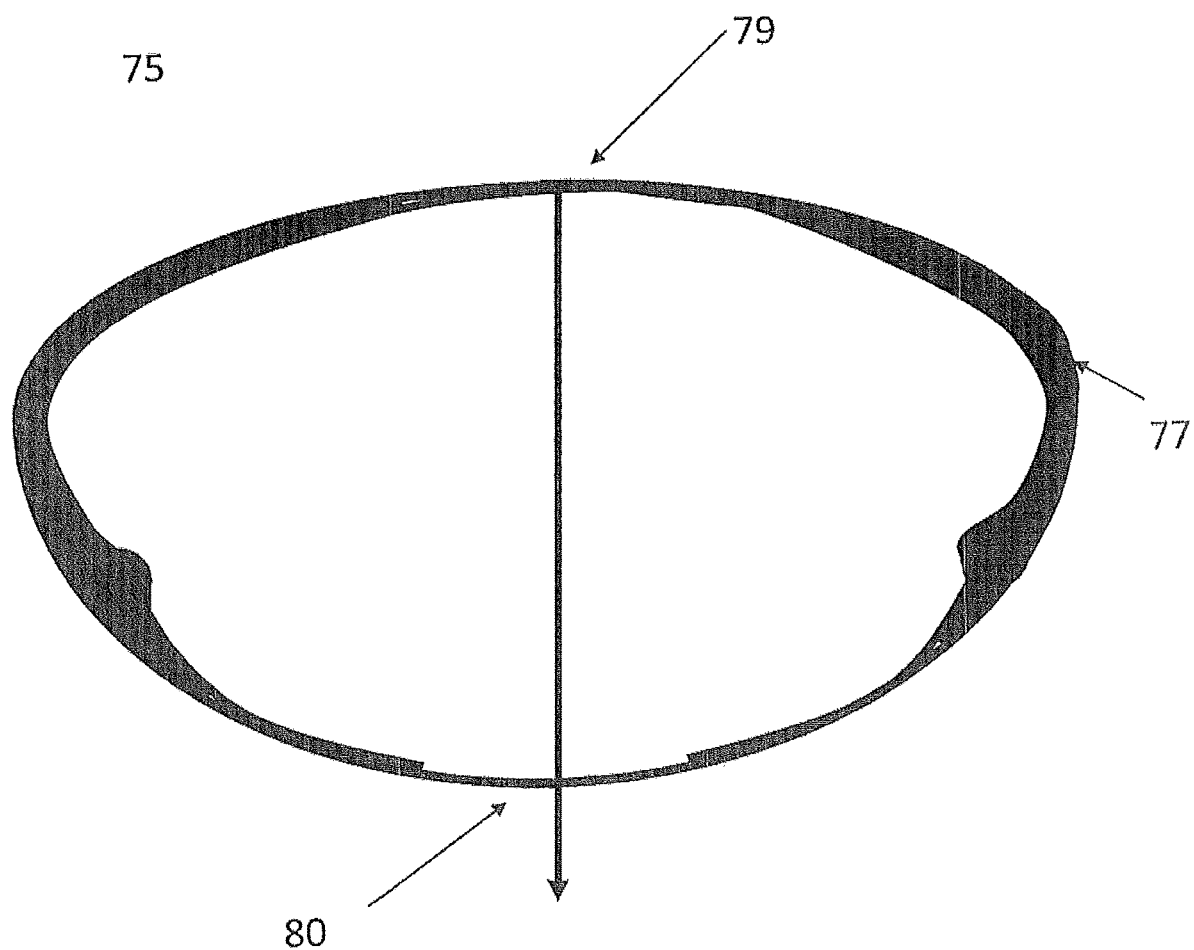
FIG. 1C is a cross-sectional view of the lens of FIG. 1A, schematically showing the wall thickness of the human lens capsule.
Figure 1D:
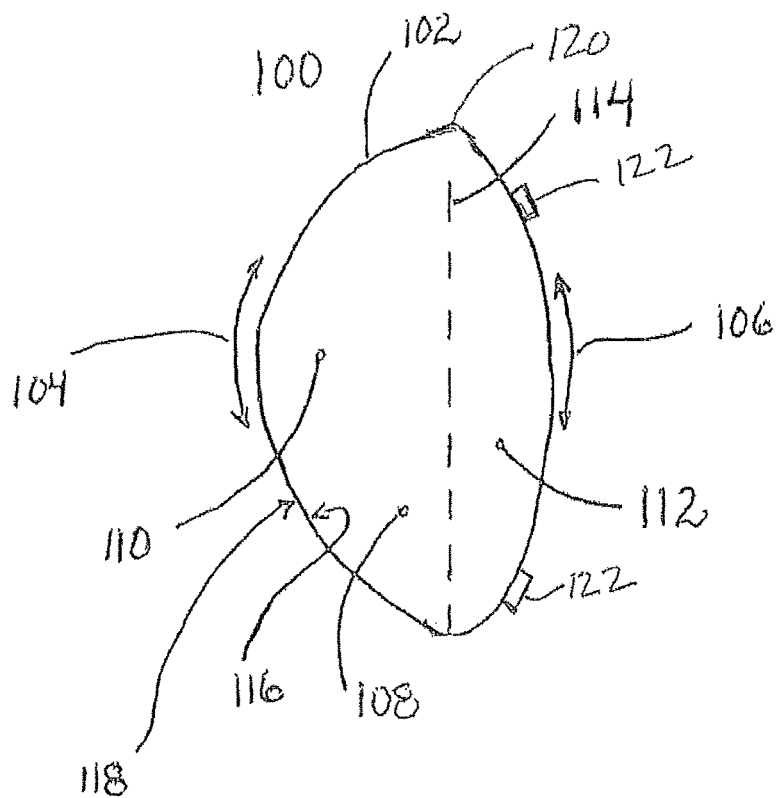
FIG. 1D cross-sectional view of an exemplary embodiment of an IOL of the present disclosure, showing the capsular interface, anterior pole shape, posterior pole shape, and an internal medium.

Reference will now be made to the drawings wherein like reference numerals identify similar structural features or aspects of the subject invention. For purposes of explanation and illustration, and not limitation, a partial view of an exemplary embodiment of an intraocular lens (IOL) in accordance with the invention is shown in FIG. 1D and is designated generally by reference character 100. Other embodiments of IOLs in accordance with the invention, or aspects thereof, are provided in FIGS. 2-6, as will be described. The system of the invention can be used, for example, to provide a crystalline lens replacement with a close functional approximation to a healthy lens.

This description begins with a description of particular embodiments of IOL devices, then attention will be directed to description of particular methods of implantation of the IOL device, and finally novel features will be described with respect to their benefit and utility in use.

IOL Device Example 1

Referring to FIG. 1D, an IOL 100 is comprised of a capsular interface 102, an anterior pole shape 104, a posterior pole shape 106, and an internal medium 108. The internal medium 108 is further comprised of anterior side 110 and posterior side 112. IOL 100 has an equatorial plane 114 which is co-planar with the interface between anterior side 110 and posterior side 112. The index of refraction of anterior side 110 is substantially equivalent to the index of refraction of posterior side 112. The capsular interface 102 possesses internal side 116 and external side 118. The intersection of the equatorial plane 114 with the capsular interface 102 is the equatorial circumference 120 of the capsular interface 102. Disposed posteriorly of the equatorial circumference 120 on the external side 118 are localization areas 122. The localization areas 122 adhere to the natural capsule, helping to center the IOL within the capsule and decreasing relative movement between the IOL and the capsule. This connects the IOL and the capsule to minimize the attachment of the natural lens to the capsule. The width 124 of localization areas 122 can range from 100 micrometers to 2 millimeters.

Figure 2:
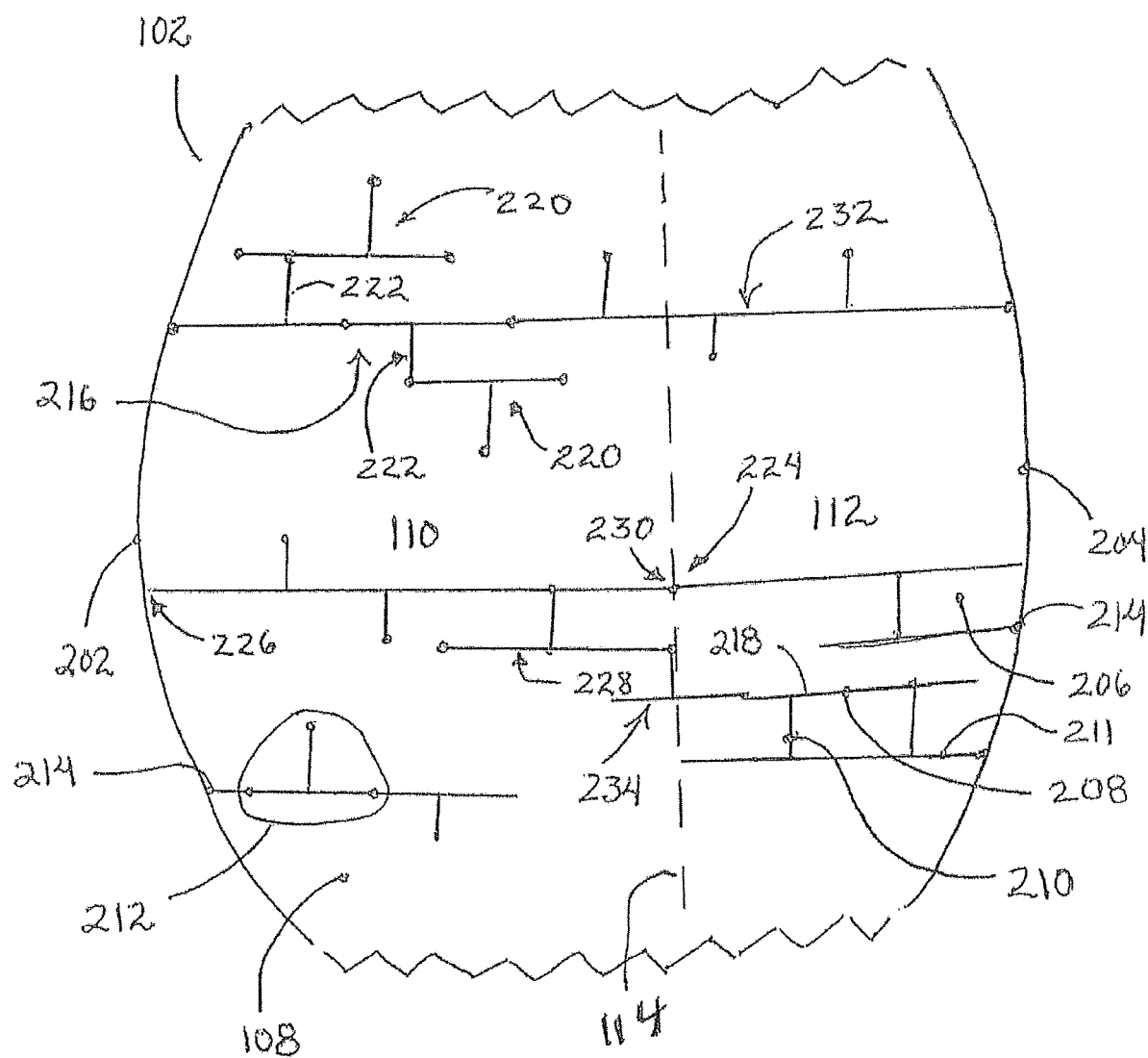
FIG. 2 is a schematic microscopic view of the IOL of FIG. 1D, showing a filling medium disposed in a capsular interface.

Referring now to FIG. 2, a magnified view of the internal medium 108 residing between the anterior 202 and posterior 204 walls of the capsular interface 102 is shown. In the preferred case, internal medium 108 is constructed of anterior side 110 and posterior side 112, alternatively the medium 108 is introduced into the capsular interface 102 all at once in a liquid state and cured to a substantially solid state in one step. The solidified polymer comprising 110 and 112 preferably is comprised of an aqueous phase 206 and a solid phase 208, wherein the solid phase 208 is a polymeric network with a select degree of cross linking. Depicted in FIG. 2 is a solid phase 208 with three-arm functionality 210 comprising monomeric units 212. These three-armed monomers 212 form extended networks when they polymerize within capsular interface 102. The external side 118 of capsular interface 102 is smooth and resists tissue ingrowth. The internal side 116 of capsular interface 102 is bonded with a thin layer of polymer active substance 214. During polymerization the monomers 212 nearest internal side 116 tend to have one of their arms 211 bond to polymer active substance 214. The remaining arms 210 polymerize to other arms 210 of other monomers 212 forming polymeric chains 216 anchored to internal side 116. Still other monomers 218 away from internal side 116 form polymeric chains 220 with no anchor to internal side 116. Polymeric chains 216 and 220 are laterally joined by a roughly perpendicular network of arms 222. There are then free ends 224 at the equatorial plane 114. If a second layer is poured, we again have bonds 226 to the opposite internal side 110 and free polymeric chains 228. During the second layer polymerization, some of the polymeric chain ends 230 in the second polymerizing layer join with free ends 224, but not all. Thus, anterior side 110 is more loosely coupled to posterior side 112, than the coupling within anterior side 110 and posterior side 112. Thus whatever shape was achieved for the anterior side 110 is somewhat decoupled from the shape achieved for the posterior side 112. In a single pour methodology the anterior side 110 is more strongly coupled to posterior side 112, since polymeric chains are in general longer and there are almost no free ends near the equatorial plane 114. In either case there will be polymeric chains 232 connecting the anterior side 110 to the posterior side 112 and free polymeric chains 234 connecting neither side 110 nor 112.

Figure 3A:
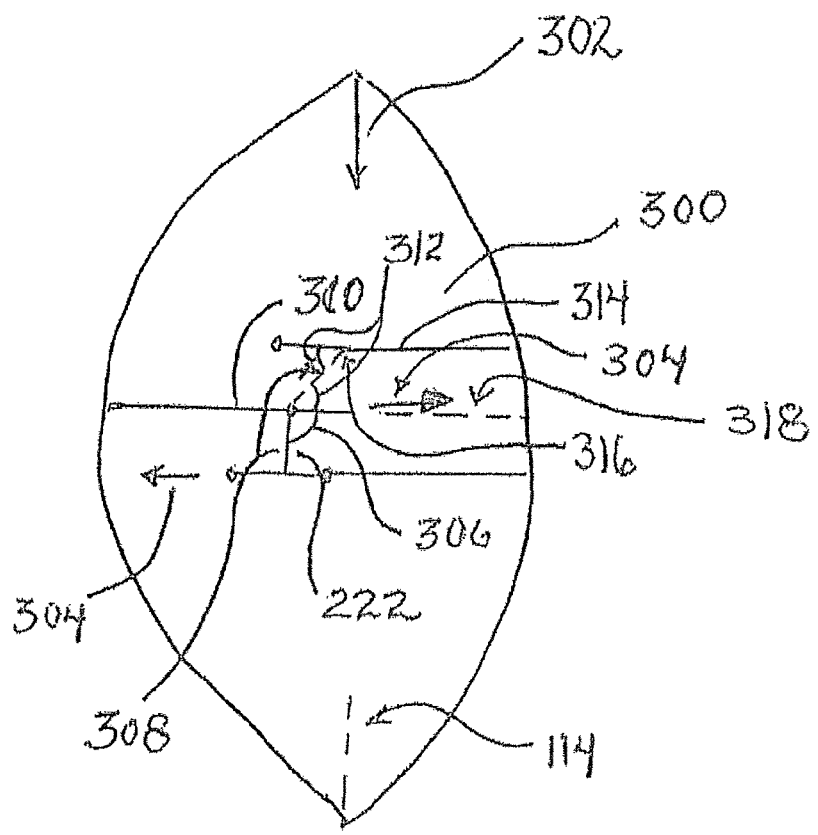
FIG. 3A is a cross-sectional view of the IOL of FIG. 1D, showing the mechanism of cranial-caudal restorative forces.
Figure 3B:
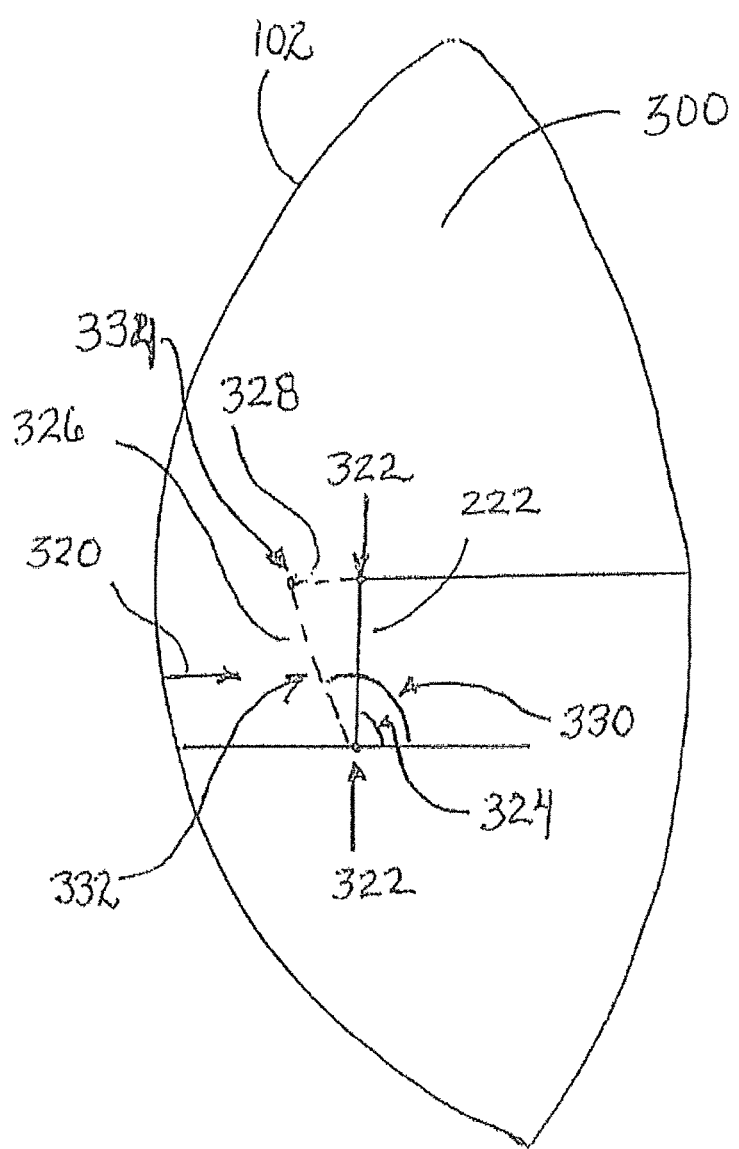
FIG. 3B is a cross-sectional view of the IOL of FIG. 1D, showing the mechanism of anterior-posterior restorative forces.

Referring now to FIGS. 3A and 3B, the polymeric structure of the fully polymerized internal medium 300 is shown. In one instance, FIG. 3A, a cranial-to-caudal force 302 is applied in representation of an approximate gravitational force. The distensible polymeric chains in bulk resist cranial-to-caudal dilation by supplying anterior-to-posterior restorative forces 304. Anterior-to-posterior forces 304 places tension on lateral arms 222 which causes the angle 306 between representative lateral arm 308 and representative axial polymeric chain 310 to decrease to angle 312 with the lateral arm position 314 and new polymeric chain position 316. Thus, while the action of gravity is unidirectional, the degree of cranial-to-caudal shortening is symmetric about axial centerline 318 and the degree of anterior-to-posterior dilation is proportionally symmetric about the equatorial plane 114. In FIG. 3B, an anterior-to-posterior force 320 is applied. This is the force applied by the capsular interface 102 to the internal medium 300 when the capsular interface is suspended within the capsule. Force 320 causes distensible polymeric chains in bulk to resist cranial-to-caudal dilation by supplying cranial-to-caudal restorative forces 322. Cranial-to-caudal forces 322 places tension on lateral arms 222 which causes the angle 324 between representative lateral arm 326 and representative axial polymeric chain 328 to increase to angle 330 with new lateral arm position 332 and new polymeric chain position 334. FIGS. 3A and 3B describe a set of restorative forces designed to keep the IOL in a preferred ellipsoidal shape under the action of gravity, while providing for accommodative changes anterior and posterior radii of curvature. Generally speaking, the concept of having both a solid phase and a liquid or lower modulus phase is intended to minimize the volume of the filling that must be affected through muscular action in order to achieve accommodation. It will be appreciated that such a multiple phase configuration may be achieved by: (1) inserting the capsular bag into the prepared space, inserting a preformed solid portion into the capsular bag, positioning the solid portion within the bag, and injecting one or more "pours" of filling material around the solid portion; (2) inserting the capsular bag into the prepared space with the solid portion pre-attached to the inside of the capsular bag, and filling around the solid portion within the bag until the desired optical properties are achieved; or (3) inserting the capsular bag into the prepared space, injecting a first material into the bag to form the more solid portion of the filling within the bag, possibly adhered to an interior surface of the bag, and injecting one or more pours of additional material around the solid portion to provide the area of lower modulus and greater deformability around the solid portion. It is contemplated that providing multiple phases and/or multiple injections of similar materials may provide greater flexibility to adjust index of refraction between materials and lens power during accommodation.

IOL Device Example 2

In some cases a patient's accommodative capacity is markedly diminished and cannot be enhanced by providing an improved accommodative gain (optical power range) or set point (optical power mean). In this case, it may be necessary to interpose within the capsular interface a solid inflexible optic. While the scope of this invention includes combining the accommodative power of shape changes in the capsular interface with anterior-posterior translations of an optic, it is generally the case that acuity and contrast is superior in the instance of the fewest refractive index discontinuities. In order for the capsular shape to increase total eye optical power it would be necessary for the index of refraction inside the capsular interface to be somewhat higher than the index of refraction of the tissue anterior or posterior to the capsular interface. Accordingly, it is preferred the capsular bag be filled with a bi-phasic flowable medium with a refractive index close to that of the surrounding tissue.

Figure 4:
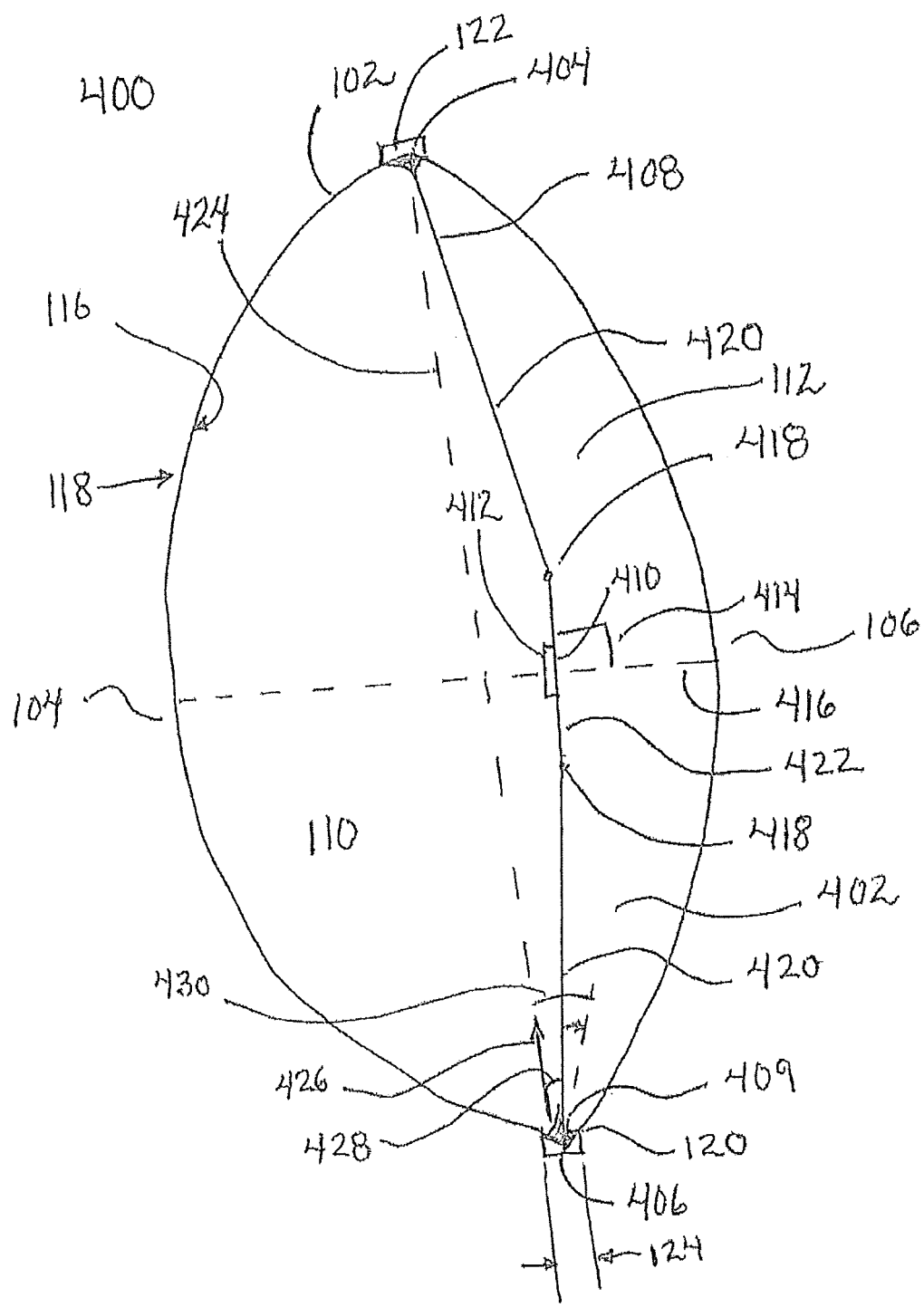
FIG. 4 is a cross-sectional view of an exemplary embodiment of an IOL constructed in accordance with the present disclosure, showing a capsular interface that possesses internal structure.

Referring now to FIG. 4, an IOL 400 is comprised of a capsular interface 102, an anterior pole shape 104, a posterior pole shape 106, and an internal flowable medium 402. The internal medium 402 is further comprised of anterior side 110 and posterior side 112. IOL 400 has an equatorial plane 424 which is co-planar with the interface between anterior side 110 and posterior side 112. The index of refraction of anterior side 110 is substantially equivalent to the index of refraction of posterior side 112 and substantially equivalent to the surrounding tissue. The capsular interface 102 possesses internal side 116 and external side 118. The intersection of the equatorial plane 424 with the capsular interface 102 defines the equatorial circumference 120 of the capsular interface 102. Disposed on the equatorial circumference 120 on the external side 118 is located localization area 122 running circumferentially along the equatorial circumference 120 of capsular interface 102. The localization areas 122 adhere to the natural capsule, helping to center the IOL within the capsule and decreasing relative movement between the IOL and the capsule. This connects the IOL and the capsule to minimize the attachment of the natural lens to the capsule. The width 124 of localization areas 122 can range from 100 micrometers to 2 millimeters. Additionally there is cranial pole 404 and caudal pole 406. On the internal side 116 of the cranial pole 404 is attached a strip of flexible, optically clear biocompatible material 408, the other side of which is attached to the internal side 116 of the caudal pole 406. Preferably, internal strip 408 and capsular interface 102 are a single molded or cast part. The connections between internal strip 408 and internal side 116 may be radiused 409 to avoid the intersection of perpendicular surfaces for improve durability. The modulus of the strip 408 and capsular interface 102 are between 0.1 and 2 MPa. Located near the center of strip 408 is a circular cutout 410 into which are bonded a conventional rigid optic 412 (not shown to scale). In order to maintain the orthogonal relation between the equatorial plane of the IOL 414 and the anterior-posterior axis of the eye 416, strip 408 contains two preferential bend points 418 on either side of optic 412. In addition, it is preferred but not necessary that distal segments 420 adjacent poles 404 be more flexible than central segment 422. Thus when the equatorial diameter 424 of the capsular interface 102 decreases 426 the angle 428 increases 430 resulting in translation of rigid optic 412 along anterior-posterior axis 416 such that angle 414 remains approximately normal throughout the potential range of translation In this way the optic shifts forward and the power of the lens increases to permit focused viewing of near objects. While the rigid optic 412 may be biased posteriorly as shown, it may also be biased anteriorly. Thus an IOL of this construction will typically have two optical power set points which are selectable during implantation. The length of strip 408 must be adequately long such that throughout the range of accommodation the position of the rigid optic 412 never crosses equatorial diameter 424. The case where rigid optic 412 crosses equatorial diameter 424 at some point in the accommodation range is addressed in the subsequent example Referring now to FIG. 5A, a labio-lingual view 500 of the internal medium 502 residing between the anterior 202 and posterior 204 walls of the capsular interface 102 is shown. In the preferred case, internal medium 502 is constructed of anterior side 504 and posterior side 506, where the thickness 508 of the posterior side 506 is less than the thickness 510 of the anterior side 504. The cured yet flowable polymer comprising 504 and 506 is comprised of an aqueous phase 206 and a solid phase 208, wherein the solid phase 208 is a polymeric network with selectable degree of cross linking. The specific weight of strip 408 is less than the specific weight of the internal medium 502 prior to gelation such that the optic 412 floats on the surface of posterior side 506 prior to gelation. The selection of thicknesses 508 and 510 establishes the optical power set point of optic 412 and provides for in vivo assessment of the focal length relative to the retina of the eye. Optic 412 is able to translate in response to a physiologic change in ciliary muscle tension due to the flowability of internal medium 502 around strip 408. It should be understood the solid inflexible optic 412 is an optional feature, and that the strip 408 may possess refractive or geometric properties along a substantial portion of it length that achieve an enhanced accommodative effect. Additionally, the inflexible optic 412 may be a localized geometric form impressed into strip 408 such that the entire strip is of one material.

IOL Device Example 3

In this example, for illustrative purposes figures of Example 2 will be reused since the features that differentiate Example 3 over Example 2 are based on dimensional differences and not structural difference.

In some cases a patient's accommodative capacity is absent and cannot be enhanced by providing an improved accommodative gain (optical power range) or set point (optical power mean). In this case, the internal optic 412 and strip 408 can be configured within capsular interface 102 to achieve a bistable state. The bistable state is achieved when the optic 402 can translate through the equatorial diameter 424. In this case, finger pressure or flexing of muscles around the eye can allow the patient to select between an anterior biased position of optic 412 and a posterior biased position of optic 412. Thus, for the fixed accommodative state of the patient's eye, there are two minimum energy configurations of the strip 408 within the capsular interface 102. These two minimum energy states correspond to near- and far-sighted accommodations of the optical power of the eye. The difference in dioptric power between these two accommodative states is a function of the length of the strip 408.

While the scope of this invention includes combining the accommodative power of shape changes in the capsular interface with anterior-posterior translations of an optic, it is generally the case that acuity and contrast is superior in the instance of the fewest refractive index discontinuities. In the present case the eye has no natural accommodative power, accordingly it is preferred the capsular bag be filled with a bi-phasic flowable medium with a refractive index close to that of the surrounding tissue.

Referring now to FIG. 4, an IOL 400 is comprised of a capsular interface 102, an anterior pole shape 104, a posterior pole shape 106, and an internal flowable medium 402. The internal medium 402 is further comprised of anterior side 110 and posterior side 112. IOL 400 has an equatorial plane 114 which is co-planar with the interface between anterior side 110 and posterior side 112. The index of refraction of anterior side 110 is substantially equivalent to the index of refraction of posterior side 112 and substantially equivalent to the surrounding tissue. The capsular interface 102 possesses internal side 116 and external side 118. The intersection of the equatorial plane 114 with the capsular interface 102 is the equatorial circumference 120 of the capsular interface 102. The localization areas 122 adhere to the natural capsule, helping to center the IOL within the capsule and decreasing relative movement between the IOL and the capsule. This connects the IOL and the capsule to minimize the attachment of the natural lens to the capsule. The width 124 of localization areas 122 can range from 100 micrometers to 2 millimeters.

Additionally there is cranial pole 404 and caudal pole 406. On the internal side 116 of the cranial pole 404 is attached a strip of flexible, optically clear biocompatible plastic 408, the other side of which is attached to the internal side 116 of the caudal pole 406. Preferably, internal strip 408 and capsular interface 102 are a single molded or cast part. The connections between internal strip 408 and internal side 116 may be radiused to avoid the intersection of perpendicular surfaces for improve durability. The modulus of the strip 408 and capsular interface 102 are between 0.5 and 5 MPa. Located near the center of strip 408 is a circular cutout 410 into which are bonded a conventional rigid optic 412. In order to maintain the orthogonal relation 414 between the equatorial plane of the IOL and the anterior-posterior axis of the eye 416, strip 408 contains two preferential bend points 418. In addition, it is preferred but not necessary that distal segments 420 be more flexible than central segment 422. Thus when a pressure is applied by the conscious flexing of facial muscles of the placement of the finger over the eye lid in either a cranial or lateral aspect, the equatorial diameter 424 of the capsular interface 102 changes 426 the angle 428 changes 430 resulting in translation of rigid optic 412 along anterior-posterior axis 416 such that angle 414 remains approximately normal throughout the potential range of translation. The direction of angle changes 428 and 430 depends on the prior state of strip 408. Therefore, if the strip 408 is in the anterior position pressure placed peri-optically causes strip 408 to be displaced further anteriorly and the rebound effect of removing the external pressure causes strip 408 to pass through equatorial plane 414 and is carried to the second energy minima in the posterior position. Conversely, if the strip is in the posterior position pressure placed peri-optically causes strip 408 to be displaced further posteriorly and the rebound effect of removing the external pressure causes the strip 408 to pass through equatorial plane 414 and is carried to the second energy minima on the anterior position. In this way a patient can readily alternate between near and far-sighted accommodation. It is clear from this mechanism that the potential energy placed in strip 408 during hyper-anterior or hyper-posterior extension of strip 408 must be sufficient to carry strip 408 through the potential energy barrier presented by the equatorial strip position. Therefore, the modulus or the overall elasticity of the flexing mechanism built into strip 408 determines the potential energy of the hyper-extension position governed by Hooke's Law. Ideally, one selects a flexural modulus that provides for the desired hyper-extension with a minimal amount of external pressure, but requires a sufficient pressure such that the position of strip 408 is not oscillating between anterior and posterior positions during normal eye movement.

It may also be desirable to bias the strip 408 to a position corresponding to near or far-sightedness, typically the far-sighted position is chosen. While the rigid optic 412 may be biased posteriorly as shown, it may also be biased anteriorly. Thus an IOL of this construction will typically have two optical power set points which are selectable during implantation.

Figure 5A:
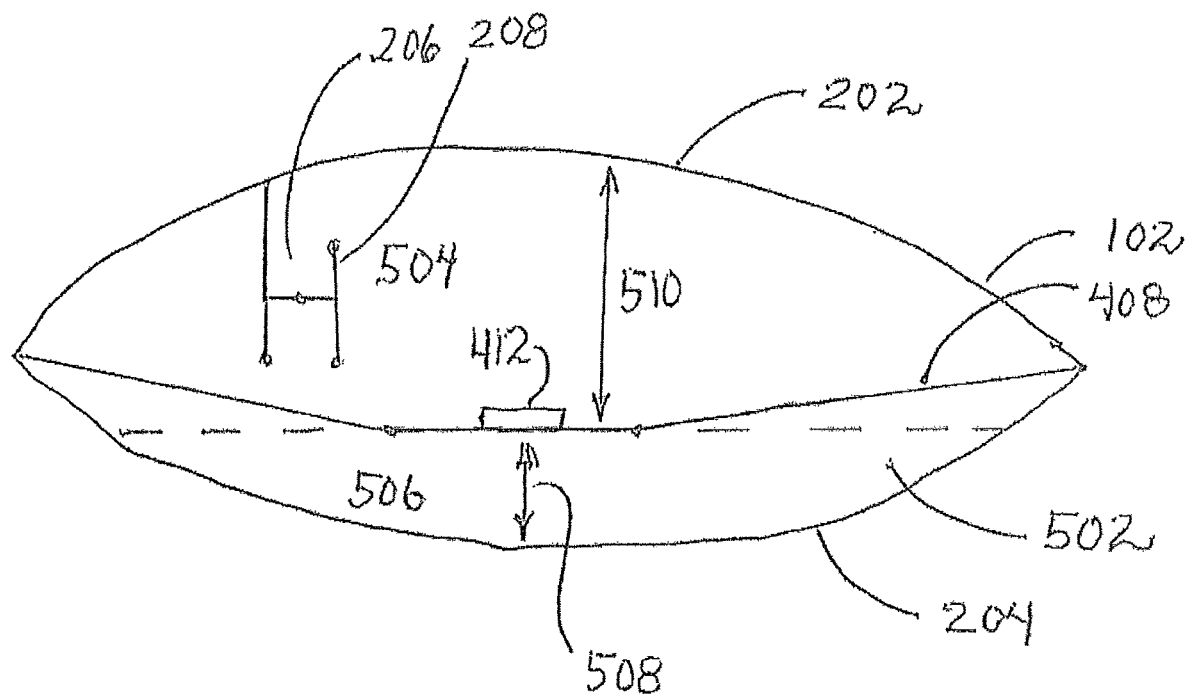
FIG. 5A is a cross-sectional view of the IOL of FIG. 4, illustrating a method of establishing the optical power set point.

Referring now to FIG. 5A, a labio-lingual view 500 of the internal medium 502 residing between the anterior 202 and posterior 204 walls of the capsular interface 102 is shown. In the preferred case, internal medium 502 is constructed of anterior side 504 and posterior side 506, where the thickness 508 of the posterior side 506 is different from the thickness 510 of the anterior side 504. The solidified yet flowable polymer comprising 504 and 506 is comprised of an aqueous phase 206 and a solid phase 208, wherein the solid phase 208 is a polymeric network with selectable degree of cross linking. The specific weight of strip 408 is less than the specific weight of the internal medium 502 prior to gelation such that the optic 412 floats on the surface of posterior side 506 prior to gelation. The selection of thicknesses 508 and 510 establishes the optical power set point of optic 412 and provides for in vivo assessment of the focal length relative to the retina of the eye. Optic 412 is able to translate in response to an external change in ocular tension due to the flowability of internal medium 302 around strip 408. It should be understood the solid inflexible optic 412 is an optional feature, and that the strip 408 may possess refractive or geometric properties along a substantial portion of it length that achieve an enhanced accommodative effect. Additionally, the inflexible optic 412 may be a localized geometric form impressed into strip 408 such that the entire strip is of one material.

IOL Device Filling Medium Example 4

In this case the capsular interface must provide structural rigidity sufficient to retain the shape of the capsular interface under different orientations with respect to gravity. In this embodiment the patient will need a relatively robust accommodative power to overcome the increased rigidity of the capsular interface, which will inherently oppose accommodative change. However, removal of an aged and stiffened lens may be sufficient to augment the accommodative aspect of the eye. In the case where the filling medium is saline, then the refractive index of the capsular bag must be chosen to mimic the power of the natural crystalline lens. Alternatively, if a nonstructural medium such as glycerin or hyaluronic acid is used the index of refraction of the capsular interface preferably matches that of the filling medium.

Maximum accommodative range is achieved when the filling medium possesses structure that mimics the natural eye. Distribution of structural integrity over the entire implant and not relying on the capsular interface to provide form reduces the required modulus of the capsular interface. A gel that retains its shape in a gravitational field does not require a stiff capsular interface. The difference between the modulus of the implant and the modulus of the natural capsule is a primary stimulus to posterior capsule opacification. Furthermore, rigid elastomers tend to be more hydrophobic than tissue, and difference in hydrophobicity is known to cause chronic inflammation.

Preferentially, the filling medium is a liquid in order to minimize delivery catheter cross section. In order to meet the dual requirements of a fluid injectable and a structure filling medium the filling medium preferentially changes state when implanted in a body. More preferred are filling agents that are capable of cross linking in the body. More preferred still, are prepolymers with two principle directions of chain extension so that a three dimensional rather than linear polymeric network is formed. One can align the polymerization direction relative to the optical axis by coating the inner surfaces of the capsular interface with a compound known to polymerize with the filling medium. The primary chains provide anterior-posterior stabilization, while the side chains provide cranial-caudal stability.

Ideally, the filling medium is permanent and retains good optical qualities after implantation. Representative synthetic, biodegradable (but permanent when implanted in a sealed capsular interface) polymerizing systems include: poly(amides) such as poly(amino acids) and poly(peptides); poly(esters) such as poly(lactic acid), poly(glycolic acid), poly(lactic-co-glycolic acid), and poly(caprolactone); poly (anhydrides); poly(orthoesters); poly(carbonates); and chemical derivatives thereof e.g., substitutions, additions of chemical groups, for example, alkyl, alkylene, hydroxylations, oxidations, and other modifications routinely made by those skilled in the art, copolymers and mixtures thereof. Representative synthetic, non-degradable polymerizing systems include: poly(ethers) such as poly(ethylene oxide), poly(ethylene glycol), copolymers of these and poly(tetramethylene oxide); vinyl polymers—poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof e.g., substitutions, additions of chemical groups, for example, alkyl, alkylene, hydroxylations, oxidations, and other modifications routinely made by those skilled in the art, copolymers and mixtures thereof.

Prepolymers of polyurethane provide durability and enhanced biocompatibility due to their tissue-like hydrophilicity, especially among the polyurea polyurethane systems. All polyurethanes are synthesized using isocyanates or their associated amines. These compounds are classed as aromatic or aliphatic. Aromatic polyurethanes tend to yellow when implanted in the body, although the use of antioxidants can diminish this tendency. It is preferred to use aliphatic isocyanates or amines because they do not yellow in the body. They are typically less stable than their aromatic counter-parts, but this is not a great concern since the filling medium is enclosed in the capsular interface.

Ideally, the prepolymer is mixed outside the body with polymerization initiators. In polyurea systems the initiator can be water. However, the action of water is to convert isocyanate functional groups in the prepolymer to amines. A byproduct of this reaction is the release of gas phase carbon dioxide. Although there are known carbon dioxide absorbers, their action is generally too slow to prevent the formation of inclusions in the polymerizing mass. Entrapped gas in the implant will create dispersion, which will dramatically decrease acuity. It is therefore preferred that the filling medium be a mixture of polymers with isocyanate end groups and polymers with amine end groups. Since the reaction between isocyanates and amines is much faster than the two step reaction of converting isocyanates to amine and then reacting the resulting amines with other isocyanatyes in the mixture, the reduction in cure time will help compensate for the generally slower reacting aliphatic isocyanates. In addition, biocompatible catalysts of tin or organic catalysts or combinations of these can be used to further increase the rate of reaction. Optimally, the mixture achieve a cohesive state within about 5 minutes of mixing the initiator with the prepolymer. Preferably, a faster reaction with a reaction time between 1 and 3 minutes is provided. Faster reactions are not preferred, and make delivery problematic. Catalysts do not change the total amount of energy liberated in a chemical reaction, but they do change the rate at which the total energy is released. In biological systems, heat energy is generally carried away by the surrounding tissue. It is temperature and not heat energy that is destructive, and typically tissue damage occurs at about 50 degrees Celsius. Therefore, it is preferred that the catalysts be chosen, if one is needed, such that the rate of reaction does not result in an elevation of tissue temperature above 50 degrees Celsius.

An example of a prepolymer system which achieves the aims of this invention consists of two parts: an isocyanate functionalized prepolymer liquid and an amine-catalyst initiator liquid, which when mixed rapidly forms an optically clear and colorless gel. Preferably, the molecular weight of the isocyanate functionalized prepolymer is above 10,000 Dalton, and more preferably above 15,000 Dalton. The base polymer can be dimethylsiloxane ethylene oxide block copolymer, for example PEG-113 dimethicone (Meryer Chemical, China). These are linear chains of copolymer with 2 pendant OH groups with total molecular weight of approximately 9000 Dalton. In order to form the prepolymer, the dimethylsiloxane ethylene oxide block copolymer is reacted with isophorone diisocyanate (an aliphatic isocyanate) in sufficient quantities to ensure encapping of the dimethylsiloxane ethylene oxide block copolymer without significant chain extension. The isocyanate functionalized dimethylsiloxane ethylene oxide block copolymer is trimerized with trimethylolpropane, which occurs spontaneously. The result is the prepolymer fraction Part A. The initiator, Part B, is simply a mixture of potassium octoate catalyst (Dabco-T45, Air Products, USA), isophorone diamine, and water. Shelf life may be improved by adding the water fraction peri-operatively. The following is a process for preparing Parts A and B.

Part A: Place a 100 g of PEG-113 dimethicone in a heated and covered reaction vessel fitted with an externally controlled stir rod. Circulate dry argon or nitrogen gas over the PEG-113 dimethicone and stir at 100 revolutions per minute, or at a rate where a vortex is present but gas is not entrapped in the stirred liquid. Heat to 60 degrees Celsius while stirring, and continue until the water content of the PEG-113 dimethicone is less than 300 ppm. Then add 4.24 g of isophorone diisocyanate and continue at 60 degrees Celsius until the % NCO drops by greater than 60% from the initial introduction of the isophorone diisocyanate to the PEG-113 dimethicone. Then add 0.61 g of trimethylol propane and continue at 60 degrees Celsius while monitoring the heat output from the reaction. When the heat output is less than 4.5 kilocalories per hour, continue to stir and heat for 2 more hours and then cool and decant into a dry glass container and cap with a head of dry gas.

Part B: Mix in a dry vessel 1.1 grams of isophrone diamine with 0.65 g of potassium octuate catalyst Dabco-T45 and 100 g of water. Mix for one hour and decant into a sealed glass container.

In the preparation of the filling medium equal parts of Part A and Part B are mixed between syringes until fully suspended. The preparation is ready to be implanted and will typically gel within 3 minutes at body temperature.

IOL Device Delivery Features Example 5

Device delivery requires 3 features: a) a minimal cross section implantation device suitable for delivering the capsular interface through a hole no larger than 3 mm in diameter, b) an implantation device suitable for delivering the filling medium in a fluid state comprising a sealing mechanism to prevent extrusion of the solidified filling medium, and c) an implantation device which when deployed in filling the capsular interface, causes the capsular interface to separate from the implantation device in a way that minimizes the likelihood of capsular disruption.

Figure 5B:
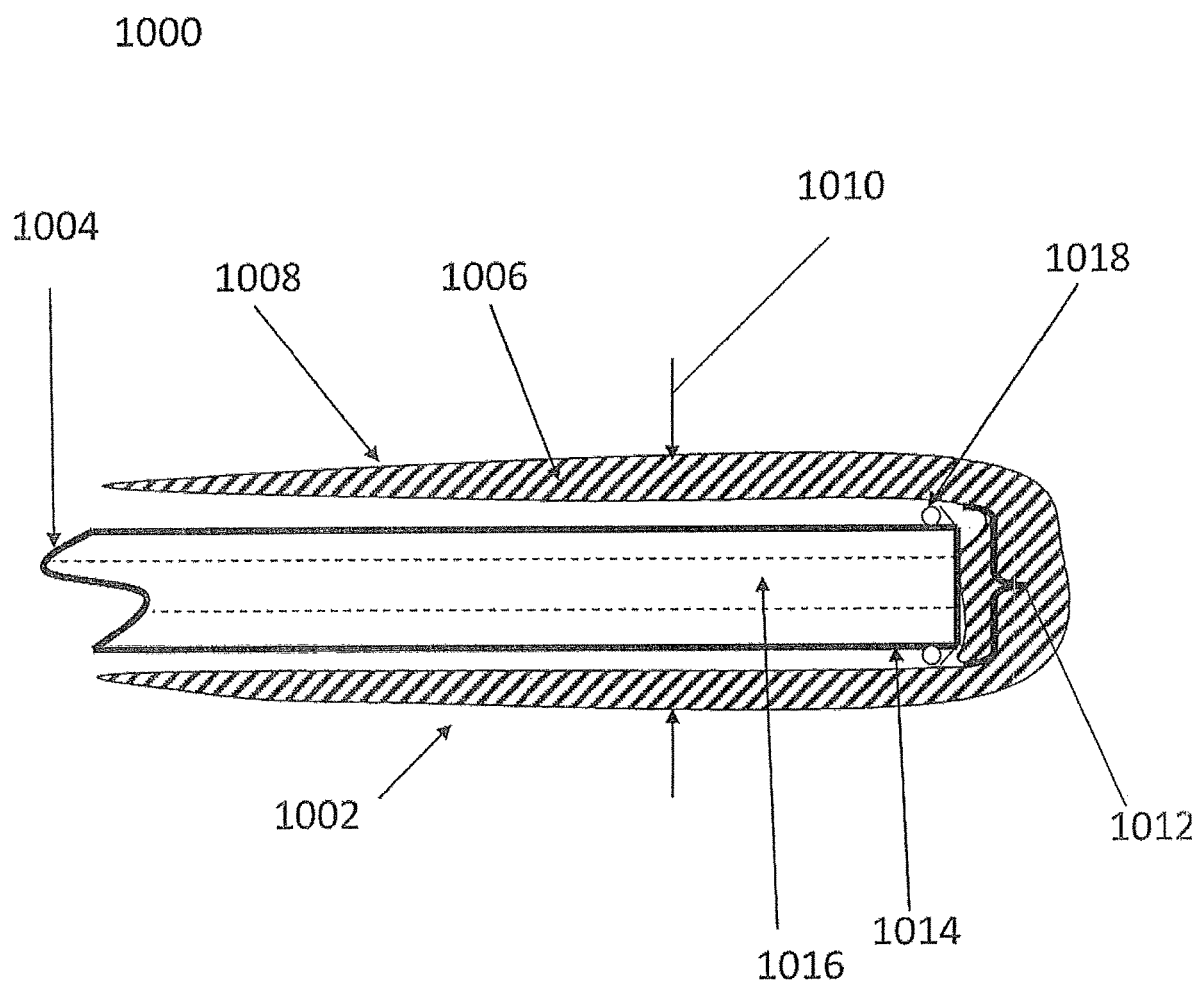
FIG. 5B is a schematic view of an exemplary configuration for implantation of a capsular interface in accordance with the present disclosure.

Referring to FIG. 5B, a configuration 1000 of the capsular interface 1002 relative to the delivery end of the catheter 1004 is shown. The capsular interface comprises internal volume 1006 (cross hatch) and external surface 1008. The capsular interface 1002 is rolled back upon the catheter 1004 causing the external surface 1008 to form an annular enveloping surface around the catheter 1004. The diameter 1010 of the combined external surface 1008 and catheter 1004 is less than 3 mm. The capsular interface 1002 is localized on catheter 1004 by means of an annular port 1012 which is stretched around the external surface tip 1014 of catheter 1004. The internal volume 1006 is fluidically connected to lumen 1016 of catheter 1004. Around the perimeter of opening 1012 the capsular interface 1002 is thicker and in the shape of a ring 1018 such that ring 1018 grips catheter tip 1014.

Figure 5C:
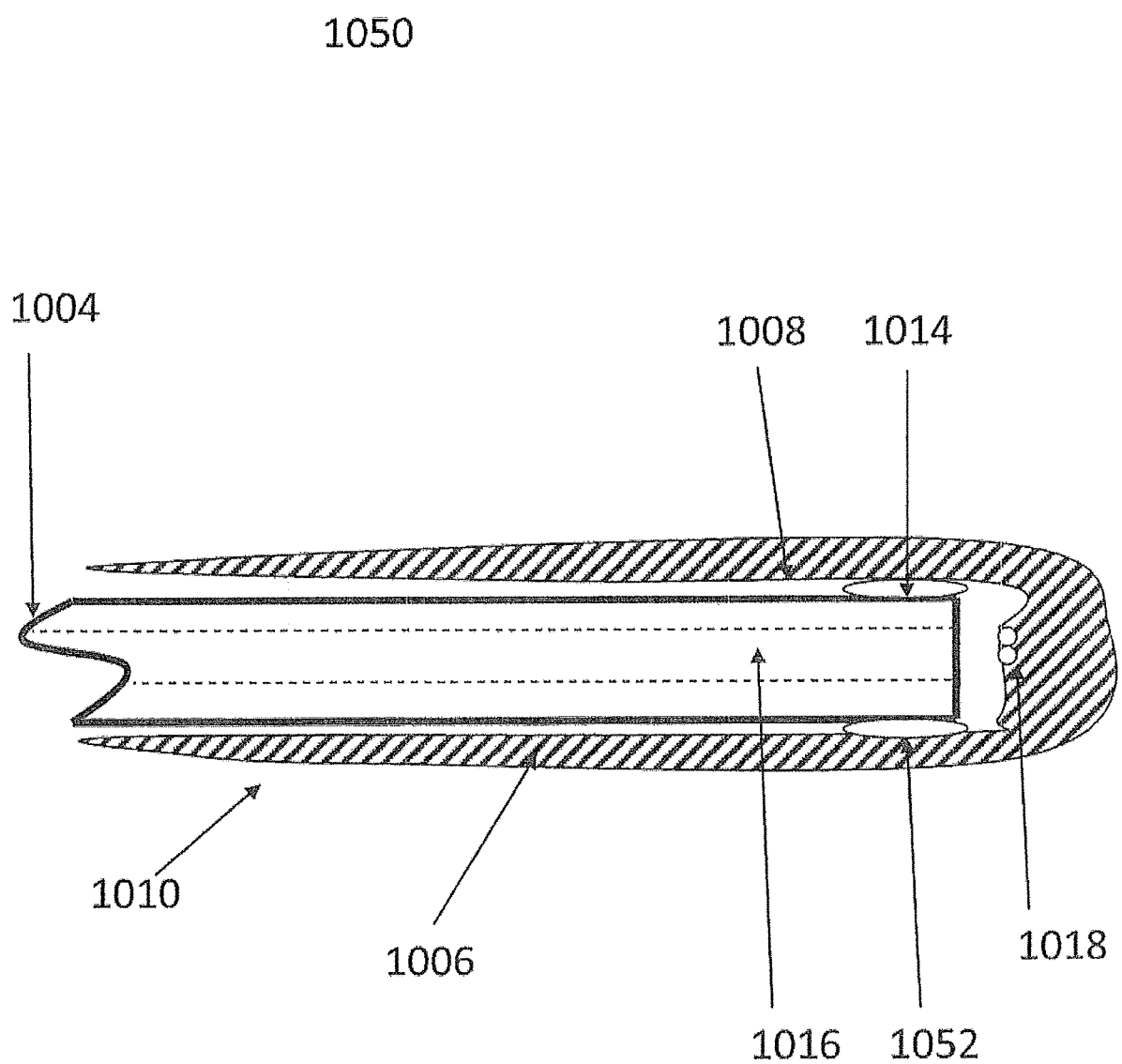
FIG. 5C is a schematic view of another exemplary configuration for implantation of a capsular interface in accordance with the present disclosure.

Alternatively, FIG. 5C shows a different configuration 1050 for retaining capsular interface 1002 to catheter 1004. Here, capsular interface ring 1018 is not stretched around external surface tip 1014. Juxtaposed between capsular interface external surface 1008 and external surface tip 1014 is tacky film 1052. The adhesive strength between the external surface of the capsular interface 1008 and external catheter tip 1014 provided by tacky film 1052 is sufficient to open ring 1018 when fluidic pressure is applied via lumen 1016 such that lumen 1016 is fluidically connected to capsular interface internal volume 1006 without fluid leaking between the external surface 1008 and external catheter surface 1014.

For both configurations 1000 and 1050, capsular interface annular ring 1018 is capable of maintaining a fluid seal after catheter 1004 is detached from capsular interface 1002. The fluid seal is achieved in configuration 1000 by pulling catheter 1004 away from capsular interface 1002 such that annular ring 1018 slides off catheter tip 1014. The fluid seal is achieved in configuration 1050 as soon as fluidic pressure in lumen 1016 is reduced to ambient.

Figure 5D:
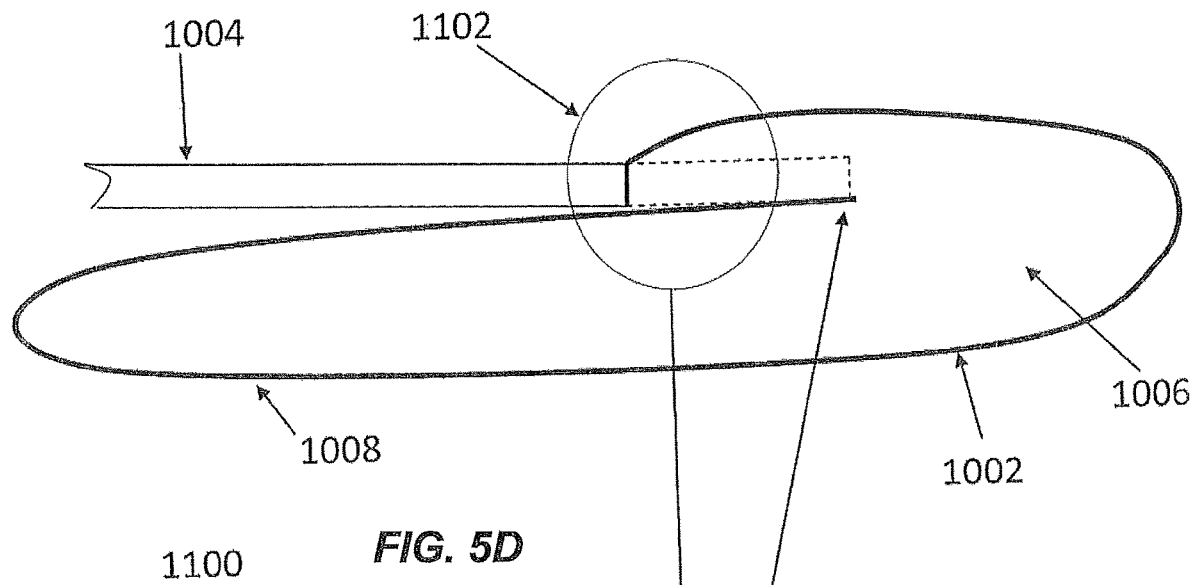
FIG. 5D is a schematic elevation view of yet another exemplary configuration for implantation of a capsular interface in accordance with the present disclosure.
Figure 5E:
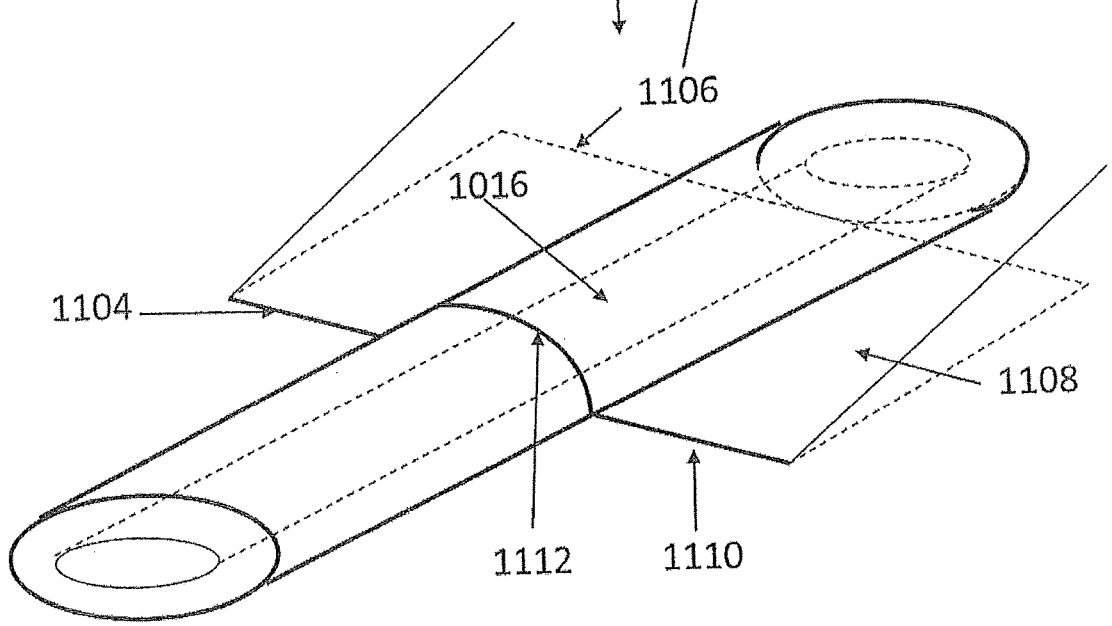
FIG. 5E is a schematic perspective view of the configuration for implantation of a capsular interface shown in FIG. 5D.

A third design 1100 for removing the fluidic connection between capsular interface 1002 and catheter lumen 1016 and fluidically sealing capsular interface 1002 is shown in FIGS. 5D and 5E. The catheter 1004 resides in a small pocket 1102 in capsular interface 1002. Pocket 1102 is comprised of leading edge 1104 and trailing edge 1106 such that the wall of capsular interface 1002 forms overlap region 1108. The leading edge 1104 is bonded to external capsular interface surface 1008 along bond line 1110 and is not bonded along port opening 1112. When catheter 1004 is inserted into port opening 1112 (as shown) port opening 1112 is fluidically sealed to catheter 1004 and capsular interface 1002 is localized on catheter 1004. Catheter lumen 1016 is fluidically connected to capsular interface internal volume 1006. While catheter 1004 is inserted in port opening 1112 edge 1112 undergoes strain. When catheter 1004 is removed from capsular interface 1002 edge 1112 fluidically seals against external capsular interface surface 1008 and overlap region 1108. To augment this sealing action overlap region 1108 may be coated with a material which will bond to the filling medium such that the entire overlap region 1108 is bonded.

The configuration of the capsular interface 1002 in design 1100 is different from the configuration depicted in configuration 1000 and 1050. In 1100 the capsular interface 1002 is wrapped around catheter 1004 obtaining a cross sectional diameter of less than 3 mm.

Figure 5F:
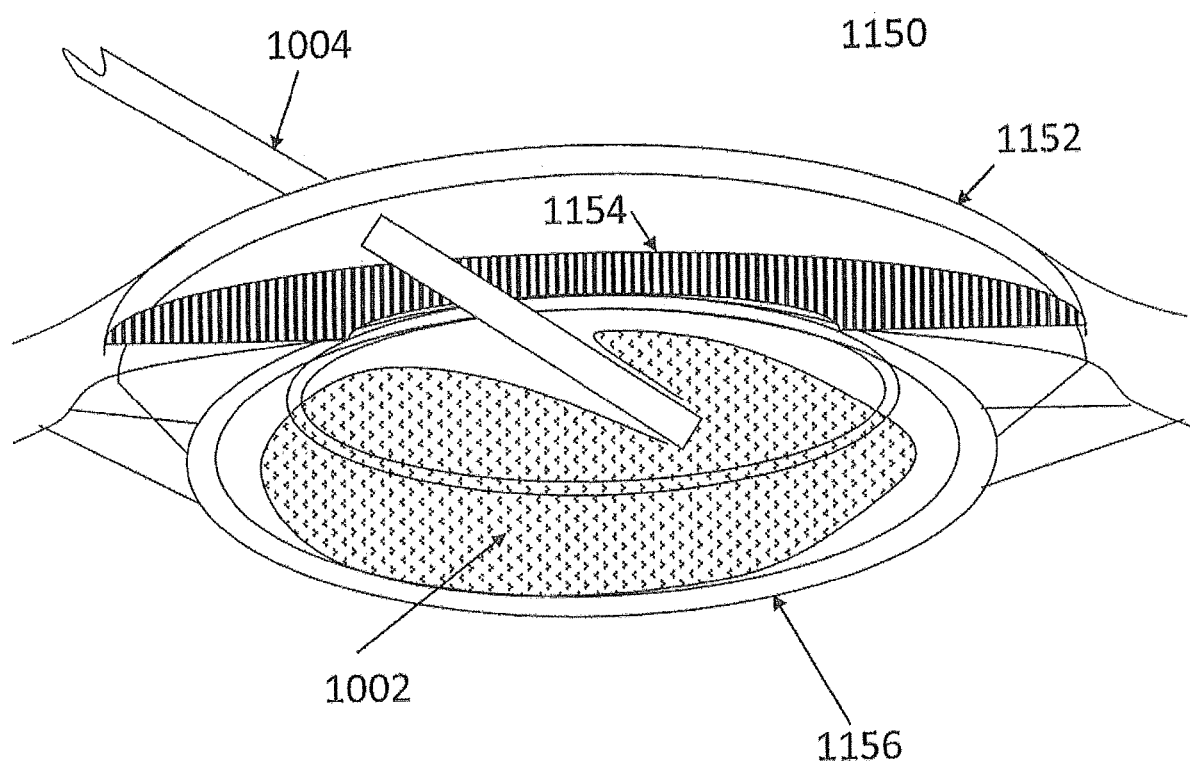
FIG. 5F is cross-sectional view of a capsular interface in accordance with the present disclosure, showing implantation of the capsular interface.

Referring now to FIG. 5F, the catheter 1004 and capsular interface 1002 are shown disposed within a human eye 1150. The principle landmarks of the eye 1150 are the cornea 1152, iris 1154 and capsule 1156. For configurations 1000 and 1050 the capsular interface 1002 rolls off catheter 1004 filling the posterior region of the capsule 1156 first. This configuration for inflating the capsular interface 1002 places minimal pressure on the anterior region of capsule 1156. A hole must be made in the capsule 1156 in order to extract the native lens and insert catheter 1004. This capsulotomy is generally made with a capsulorrhexis procedure by making a cut in the anterior surface of capsule 1156, tearing the central free flap in a circular motion to peel a continuous circular tear in the anterior capsule. The present configuration provides a means for inflating the capsular interface 1002 with minimal stress placed on the anterior surface of the capsule 1156.

For configuration 1100, the capsular interface 1002 does not roll off the tip of catheter 1004 but unwinds in circumferential fashion. This configuration may be preferred by some clinicians since the deployment of the capsular interface 1002 may be accomplished without inflating the capsular interface 1002 by rotating catheter 1004. It should be apparent that either configuration of capsular interface 1002 relative to catheter 1004 is adaptable for any of the aforementioned three sealing configurations.

The annular ring 1018 of configuration 1000 and 1050 is designed to fluidically seal when the annular ring 1018 is disconnected from catheter 1004. The amount of strain required to achieve this feature may create enough force between annular ring 1018 and catheter 1004 that for some capsular interface materials it may be difficult to detach catheter 1004 from capsular interface 1002.

Figure 5G:
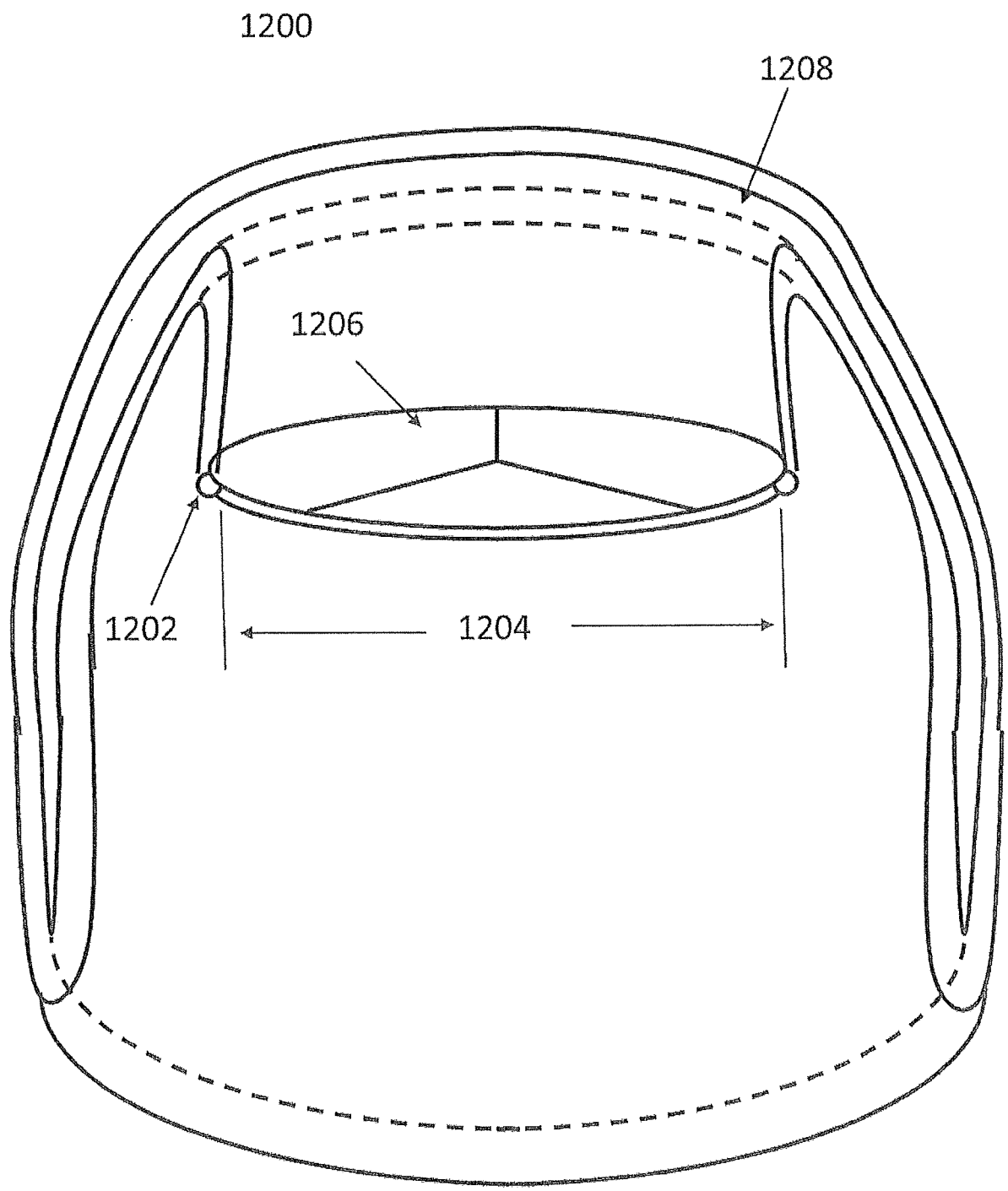
FIG. 5G is a cross-sectional perspective view of an exemplary sealing configuration decoupled from a localization function in accordance with the present disclosure.

Alternatively, the localization function of annular ring 1018 may be decoupled from the sealing function as shown in configuration 1200. FIG. 5G depicts capsular interface 1002 as it would look in configurations 1000 or 1050. The primary difference between configurations 1000 and 1050 and the depicted configuration 1200 is that annular ring 1202 is in a normally open position with diameter 1204 slightly less than the outer diameter of the mating catheter. Within diameter 1204 is tri-leaflet valve 1206. The number of leaflets is generally unimportant, but may be made greater to achieve a lower resistance to decoupling between catheter 1004 and capsular interface 1002. When capsular interface 1208 is decoupled from a catheter valve 1206 is closed.

Figure 5H:
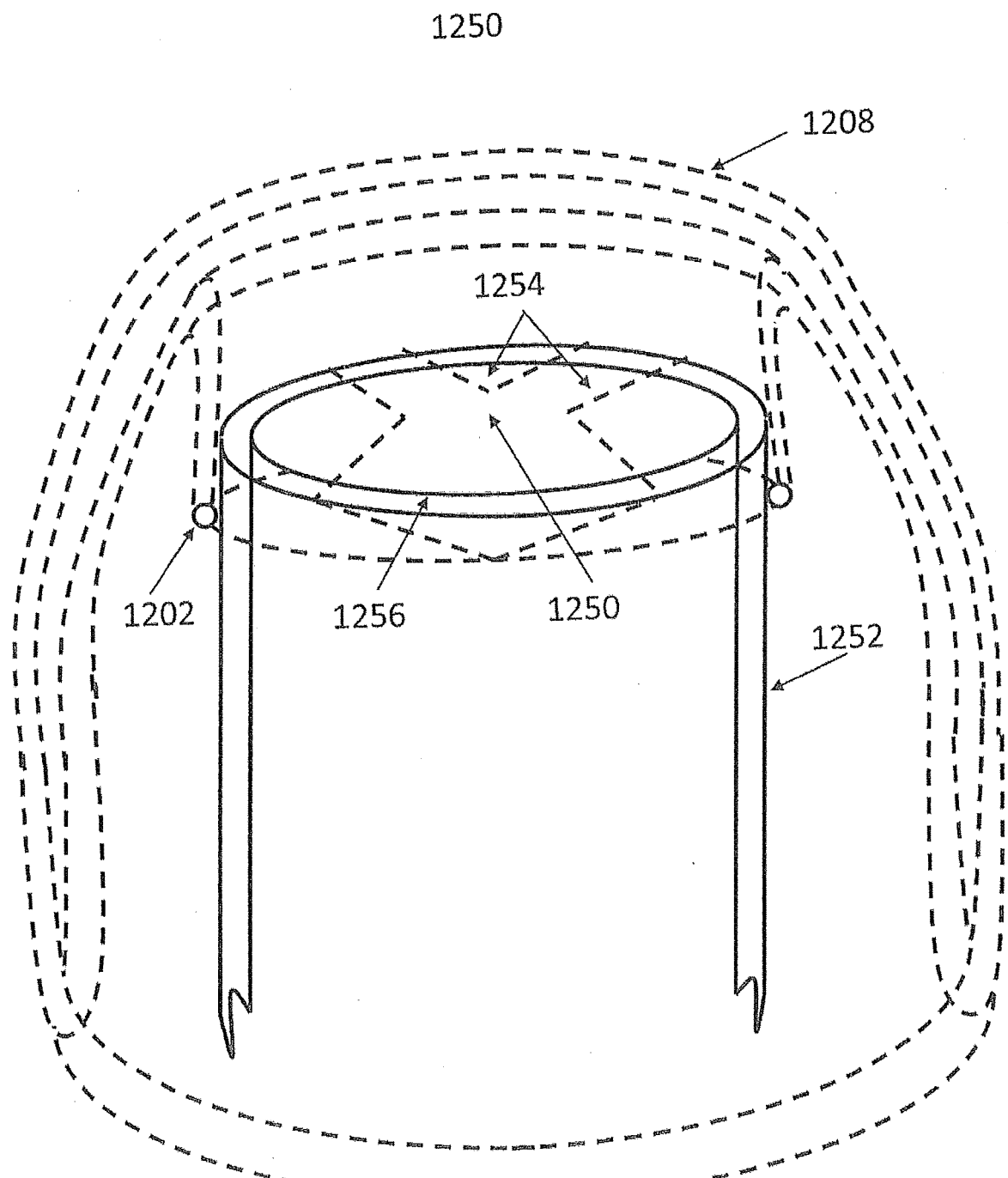
FIG. 5H is a cross-sectional perspective view of the sealing configuration of FIG. 5G, showing the function of the sealing configuration when a delivery catheter is inserted into the capsular interface.

The action of the tri-leaflet valve 1250 when catheter 1252 (solid) is inserted in capsular interface 1208 (dashed) is shown in FIG. 5H. Catheter 1252 is inserted into annular ring 1202 pushing apart leaflets 1254 and stretching annular ring 1202. Catheter lumen 1256 is fluidically connected to capsular interface 1208 and catheter 1252 is fluidically sealed to annular ring 1202.

IOL Pre-Operative Method Example 6

This example concerns pre-operative accommodation determination of the patient's eye and set point selection of the IOL of the present invention. Methods of accommodation assessment are known in the field, and must be performed when the eye is not pharmaceutically disposed to a particular accommodative state. This information is useful in selecting the IOL set point, accommodative gain, and accommodative range. The selection of the set point is done best in consideration of these and other IOL features.

The set point can be set for a near or far-sighted accommodative state, usually a far sighted accommodative state corresponding to a relaxed state of the ciliary muscles. However, the normal state of a pathologic eye may be a better set point selection. The set point is the optical power of the eye in the desired normal state.

The set point is selected by a combination of refractive index of the filling medium and level of the posterior filling thickness 508. The selection of optical power under these conditions is straightforward calculations in the art. However, appreciation of the accommodative state of the patient's eye prior to implantation is a consideration in selecting accommodative gain and accommodative range. In general, there are a variety of combinations of filling medium refractive index and posterior filling thickness which will produce a single desired optical power set point. In any case, the optical power set point is determined by the following procedure:

1. Decide on a particular set point power based on the patient's pre-implantation accommodative state.
2. Using $$\phi = \frac{1}{f} = (n-1.33)\left[\frac{2}{R_1} - \frac{(n-1.33)d}{nR_1^2}\right]$$

And substituting the desired set point power for φ, calculate R1 for d=0. All of the IOL embodiments of the present invention have d approximately equal to zero.
3. Determine the volume of filling medium required to obtain R1. In general, this is a function of a number of IOL parameters, but these calculations are routine in the art.
4. Then the desired set point is approximately obtained when posterior side 508 comprises one half of the calculated filling volume.

IOL Pre-Operative Method Example 7

This example concerns selection of accommodative gain of the IOL of the present invention. The accommodative gain is the degree of change in φ when R1 is changed. In a patient, the accommodative gain is readily measured by measuring the optical power of the eye, or alternatively the focal length, and the anterior radius of curvature of the crystalline lens when the ciliary muscles of the eye are dilated and when the ciliary muscles of the eye are contracted. A more precise approach is to measure both the anterior and posterior curvatures of the crystalline lens. Performing these measurements yield a result $$\frac{\Delta\phi}{\Delta R_1} = \gamma$$

where Δφ is the range of optical power measured (accommodative range), $\Delta R_1$ is the range in anterior crystalline lens curvature, and γ is the accommodative gain.

It should be clear to those in the art that a normal range of values for accommodative gain can be empirically derived with which to compare a pathologic instance of accommodative gain. Let $\gamma_o$ be the normal accommodative gain, $\gamma_p$ be the accommodative state of a patient, and $\gamma_{IOL}$ be the accommodative gain of the implanted IOL, then to return a patient to a normal accommodative state $\gamma_{IOL}$ must be selected such that $$\gamma_{IOL}\gamma_p = \gamma_o$$

is satisfied. Now the gain of the IOL is given by $$\gamma_{IOL} = \frac{\Delta\phi}{\Delta R_1} = (1.33-n)\left[\frac{2}{R_1^2}\right] = \frac{\gamma_o}{\gamma_p}$$

where n is the refractive index of the filling medium and R1 is the anterior radius of curvature of the capsular interface for a given filling volume. Thus n can be adjusted to satisfy a desired filling volume or conversely to determine a desired accommodative state $\gamma_{IOL}$.

IOL Volume Set Method Example 8

In general practice injection volume can be selected prior to surgery based on average experience or more precisely upon the patient's pre-treatment accommodative state. In what follows is described a peri-operative procedure for adjusting injection volume to a particular desired state of the IOL.

This example concerns selection of injection volume of the IOL and the suspension of the present invention. As describe previously, a novel aspect of the present invention over prior art IOL's is the preferred option to suspend the capsular interface within the capsule of a natural eye. Suspension, as opposed to compression, fitting of the IOL in the capsule of a natural eye enhances in the former case and degrades in the later case the accommodative range of the eye. In the preferred embodiments, the equatorial circumference of the capsular interface is lined on its exterior surface with a thin band of porous material designed to promote localization. Peri-operatively, proteinaceous fluids are present in the lens capsule after removal of the fibrous lens which interact with this localization band to fix the capsular interface to the cranial and caudal extremes of the capsule of the natural eye. While the patient is in a recumbent position, the juxtaposition of the localization band of the present invention with the desired extreme locations of the natural capsule is automatically achieved when the filling medium is introduced into the capsular interface. The pressure of the filling medium will ensure proper apposition of the tissue to the device and rapid fixation. In general, fixation will occur before the process of filling the capsular interface with medium is complete. This fixation is a desired step before proceeding with final selection of the volume of the filling medium.

In general, the clinician optimizes between optical power set point, accommodative gain and accommodative range. The accommodate gain γ and range Ω are correlated in the following way:

$$\gamma_{IOL} = \frac{\Omega_{IOL}}{\Delta R_1} = \frac{\Omega_o}{\Delta R_o}\frac{\Delta_P}{\Omega_p}$$

where $\Omega_o$, $\Delta R_o$, $\Delta R_p$, $\Omega_p$ determine optical power set point. Once determining optical power set point, then accommodative gain $\gamma_{IOL}$ and range $\Omega_{IOL}$ can be optimized such that $\Delta R_1$ satisfies $$\gamma_{IOL} = \frac{\Omega_{IOL}}{\Delta R_1}.$$

Once $\Delta R_1$ is determined, standard optical equations can be used to determine the injection volume.

IOL Accommodation Set Method Example 9

In general practice optical power set point, accommodative gain, and accommodative range can be selected prior to surgery based on average experience or more precisely upon the patient's pre-treatment accommodative state. There are a variety of ways to achieve these end points, but with respect to a simplified implantation kit designed to treat most patients the injection volume is preferably fixed as is the material of the capsular interface. Consequently, the principle means for adjusting accommodative power will be selection of the appropriate index of refraction from a set of standardized separately packages filling media. Since in this simplified implantation kit only one parameter (index of refraction of the filling medium) will be tailored to the patient, the clinician must select a target value among optical power, accommodative gain, and accommodative range. In practice, it is anticipated that generally the clinician will select an accommodative gain sufficient to allow the natural accommodative response of the eye to achieve near perfect optical power and accommodative range. This will allow for perfect acuity for both near and far accommodation. In what follows is described a peri-operative procedure for adjusting injection volume to a particular desired state of the IOL.

This example discloses methods of implantation in peri-operative adjustment of optical power set point, accommodative gain, accommodative range and injection volume. There are many aspects to the relation between a natural lens and the surrounding optical structures of a natural eye, and these are known generally in the art. For example, it is desirable to select an injection volume that does not result in the natural capsule of the eye in contact with the iris. More generally, it is desirable to the fill the IOL of the present invention such that the natural flow of aqueous human anterior to the IOL is not altered and the intraocular pressure of the eye is within a normal range.

Accordingly, implantation of the present invention comprises the following steps:

1. (Optional) It is standard practice to fill the capsule of the eye with a viscoelastic fluid (Healon®, sodium hyaluronate, Abbott Medical, USA) prior to placement of an IOL to deepen the anterior chamber and to open the capsular bag. This practice does not interfere with the steps listed here, but one should expect a substantial portion of the fluid to flow out of the capsule as the capsular interface is filled.
2. Prepare an introducer comprising the following features: a blunt distal end, a hollow shaft, a proximal end fitted with luer-type connection, to which is attached a syringe filled with saline.
3. Mount the capsular interface on the introducer element that provides for minimal cross section during introduction of the rolled capsular interface into the natural capsule of an eye. The mount should provide fluid connection between the capsular interface and the syringe.
4. Deploy the capsular interface within the natural capsule of the eye by slightly inflating the capsular interface with saline. Provide enough saline to cause the equatorial perimeter of the capsular interface to be in juxtaposition with the equatorial circumference of the natural capsule of the eye. This begins the suspension process whereby the capsular interface bonds to the posterior surface of the natural capsule adjacent but posterior to the equatorial plane of the natural capsule of the eye.
5. Once the capsular interface is stably located within the natural capsule the fluid may optionally be withdrawn and replaced by a fluid with the selected index of refraction, or optionally this fluid may be used initially.
6. The surgeon then places a beam of light through the IOL and images the beam on the fundus. The surgeon can then monitor the focal extent of the beam as the IOL is inflated.
7. During IOL inflation, the surgeon can check with regard to various physiological aspects and as well optical aspects achieved as a result of filling the IOL to a level corresponding to the posterior filling volume.
8. Subsequently, the surgeon can fill the IOL to its full target volume and check anatomical and optical features.
9. Subsequent to these checks, the surgeon withdraws the medium and prepares the final filling medium.
10. Steps 5-7 are repeated, providing for polymerization of the filling medium between steps 6 and 7.

IOL Capsule Repair Method Example 10

Occasionally, during capsulorrhexis creation, lens removal, IOL delivery and other surgical manipulations the natural capsule of the eye tears. This risk is enhanced for capsular interfaces which are rigid or include internal structure. One advantage of the present invention is that the natural capsule of the eye is filled to a normal physiologic volume. This has several beneficial outcomes, the principal benefit being the restoration of a natural volumetric and baric relation between the aqueous and vitreous humor of the eye. However, in the case of a peri-operative capsular tear the natural form introduced by inflating the IOL of the present invention provides a convenient surface on which to repair such a tear. In many cases the natural bonding that occurs between implant and living tissue allows for natural healing of the tear because the torn ends can be place in juxtaposition on the implant form. Since the implant retains this form, the pressure applied to the torn region could be quite small, provided the tear is somewhat distant from the equatorial circumference of the capsule. Alternatively, various absorbable or non-absorbable tissue adhesives could be used sparingly to hold the tissue in place during healing.

IOL Revision Method Example 11

There is a plethora of reasons why an implant may need to be removed. In most cases the IOL of the present invention can be removed in the same way the natural lens is removed within the capsule of a natural eye. In most cases, the filling medium of the capsular interface can be removed by gentle suction without the need for emulsification. In some cases, the capsular interface will need to be removed. In this case the capsular interface is deflated and drawn into a catheter or rolled to a reduced cross section around a pick device.

With respect to the localization pads of the present invention, these can be designed with an open cell porosity which will provide anchoring without attachment to the pad substrate. The substrate is preferably hydrophilic but resistant to protein deposition and attachment. Polyurethane foam is a suitable material. Restriction of the localization mechanism to the porosity of the pad, and by controlling the amount of substrate material between adjacent pores provides controllable tear strength. Thus if removal is required, a thin layer of the substrate of the pads is torn away releasing the IOL. The combination of being located far from the center of view, small discrete size, and hydrophilicity of the pad substrate ensures any tissue reaction is minimal and local.

In the case of posterior capsule opacification, the standard method of treatment is Nd:YAG laser posterior capsulotomy wherein the focus of the laser beam is placed slightly behind the posterior surface of the capsule and tissue is ablated. There may be additional ablations where the focus is successively moved anteriorly until the desired puncture is achieved. Although the posterior wall of the capsular interface is adjacent the posterior surface of the natural capsule, the treatment laser wavelength, which is typically around one micron, will not damage the capsular interface and will be preferentially absorbed by the natural capsule. Light anterior to the focal point will be absorbed by the filling medium, but neither the energy density nor the wavelength is sufficient to disrupt the polymeric structure of the filling medium. The absorption of laser light by the filling medium is insufficient to render ineffective the ablative efficacy of the laser at the focal point. Therefore, the standard method of laser ablation to remove posterior opacity of the capsule is not contra-indicated in patients receiving the devices of the present invention. However, the etiology of this condition is believed to be reduced or eliminated in the present invention since implants described herein provide for lubricious contact between the capsular interface and posterior surface of the capsule, the implant is designed to follow capsular movement rather than abrade against it, and the material of the capsular interface is more hydrophilic than most IOLs and less likely to induce fibrosis. Furthermore, if a laser should be focused in the interior of the filling medium, while the medium is structure it contains an aqueous phase. Any change in clarity of the filling medium at the point of the laser focus is likely to dissipate out of the field of view.

The following is a list of the general features of the present invention which may be modified to achieve configurations selectable for particular patient needs.

Capsule Interface

One of the primary objects of the present disclosure is to provide an IOL which does not work against accommodation and avoids applying a radial force directed outwards near the equatorial plane of the capsule.

The material of the capsule interface may be polyurethane, silicone, polyether ether ketone (PEEK) or any colorless organic polymer thermoplastic and mixtures thereof. The capsular interface may be formed by injection mold, solution cast, reaction in mold, thermal injection, and other methods for forming plastic. In particular, solution casting on a mandrel utilizing a prepolymer such that the layer formed on the mandrel is high cross linked provides exceptional durability. If a polyurethane is used an aliphatic polyurethane is preferred over an aromatic polyurethane due to the latter's propensity to yellow. Aromatic polyurethanes tend to be more durable and anti-oxidants can be used to minimize the occurrence of yellowing. In general, a slightly tinted plastic will not be noticed by the patient provided there are no inclusions or bubbles in the plastic.

One of the objects of the present disclosure is to provide an IOL that does not interfere with accommodation. The eye accommodates by reducing the equatorial axis of the natural capsule of the eye. As a result, the equatorial circumference of the capsular interface needs to decrease in length in order to follow accommodation. The capsular interface should be extremely elastic and thin walled, preferably between 1 and 25 microns in thickness. Generally one selects a capsular interface with an equatorial diameter less than the equatorial diameter of the natural capsule, preferably with a circumference 5-15 percent less than the inner surface of the corresponding natural capsule. When the capsular interface is implanted it is subsequently filled with liquid. The action of gravity may cause the liquid to spread and thus exert radially directed force which may tend to stretch the capsular interface, putting the entire surface in tension. This achieves two aims: 1) when in addition the capsular interface bonds to the equatorial circumference of the natural capsule the capsular interface becomes suspended within the natural capsule and when the patient is standing the forces applied on the suspensory ligament through the natural capsule are directed radially toward the center of the lens, and 2) accommodation by the ciliary muscles causing them to contract and thus relaxing tension in the zonules results in the tension in the capsular interface to reduce and accordingly the equatorial diameter reduces.

Figure 6:
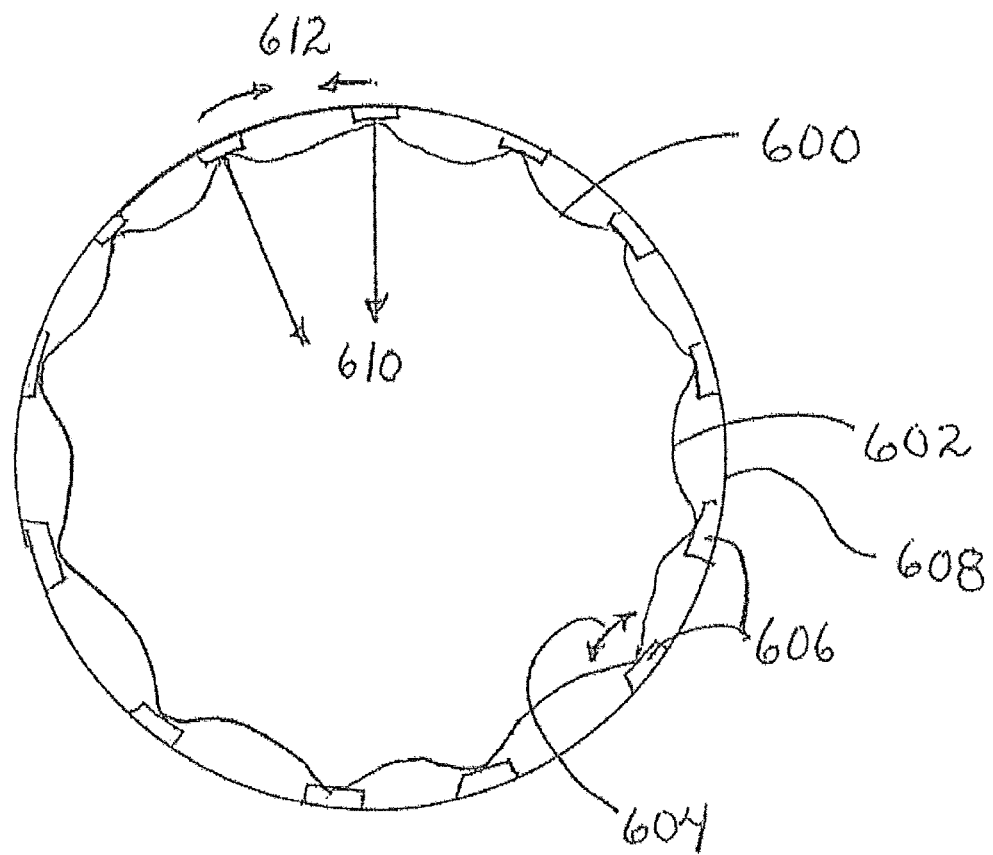
FIG. 6 is a plan view schematically showing exemplary features for localizing an IOL in accordance with the present disclosure within the natural capsule such that the IOL is suspended rather than compressed.

In addition, or alternatively, the capsular interface can be made to reduce its diameter or circumference without inducing folding at the periphery by providing for a corrugated peripheral structure. Referring to FIG. 6, capsular interface 600 is shown in sectional view taken perpendicular to the axis of the lens. The periphery 602 is the join between anterior and posterior halves of the capsular interface 600. Molded into the form are scallops 604 with localization pads 606 located at the maxima of the scalloped pattern 604. Alternatively, especially where localization of the equator of the present invention relative to the equator of the capsule is difficult or impractical, the pads are placed posterior to the capsular interface equator. This is a preferred position since it will be less likely it will interfere with accommodation. The capsular interface 600 bonds to the inner surface of the natural capsule 608 selectively at the localization pads 606. Accordingly, as the natural capsule 608 naturally contracts 610 the distance 612 between adjacent localization pads 606 reduces. This structure provides a low stress means to provide for natural accommodation, and further reduces any resistance to natural accommodation. Preferably, corrugations are formed outside the optical pupil so as not to distort the image perceived by the eye. In this manner the corrugations outside the viewing pupil facilitate deformation of the portion of the capsular bag outside the viewing pupil to accommodate the change in shape of the lens during accommodation. It is also contemplated that similar effects could be achieved by forming different portions of the bag from materials having different properties. For example, the area of the bag within the viewing pupil area may be made of a material that is less elastic than the portions of the bag outside the field of view. In this manner the portions of the bag outside the field of view which are more elastic may stretch during accommodation to change the shape of the bag, while the bag surface within the viewing pupil is not distorted and so does not alter the optical properties of the bag within the viewing pupil.

As described herein, the capsular interface has a degree of elasticity so that as the ciliary muscles flex, the capsular interface filled with filling material alters shape to act as an accommodative lens. The optic defined by the capsular interface filled with filling material starts with a defined optical power, which is altered as the device changes shape in response to the action of the muscles. That is, with the capsular interface inserted into the capsular space and filled, the shape and material (e.g., index of refraction) of the capsular interface, together with the index of refraction of the filling medium defines a lens of precise optical power. In one embodiment, a range of capsular interface devices are provided so that the surgeon, either before or at the time of surgery, selects the appropriate capsular interface material and shape which, when filled with the filling material, will provide a optic of the desired optical power for the particular patient's anatomy. Thus, the final, biconvex shape of the capsular interface could vary, depending upon the exact optical power desired of each lens. In this way, the lenses could come in a variety of shapes, and thereby in a variety of refractive powers. In addition, the capsular interface materials selected could each have a slightly different index of refraction. This variety could allow for the creation of lenses with similar shapes, but with different optical powers, depending upon patient requirements. Finally, the capsular interface could extend inside the lens, to create complex layering (honey-combing) inside the body of the lens, which could allow for various dioptric powers of the lenses. In a further embodiment, the capsular interface is made of multiple layers of material, which may be made of the same material or two or more different material, which define physical characteristic or shapes which at least in part define the optical power of the device. Thus, the various layers may be made of materials of different indices of refraction to help define the power of the device. Alternatively, or in addition, the multiple layers could include shapes, grooves, etc. to add optical power to the optic.

Centering Mechanism

The centering mechanism is largely based on the volume of the IOL relative to the volume of the capsule, which in the preferred case is nearly equal. In this case, pressure from the aqueous and vitreous humors as well as the suspensory ligament are naturally equilibrated. In the prior art, the replacement lens is substantially less volume than the natural lens, this depressurizes the aqueous and vitreous humor and reduces their ability to provide the usual centering mechanism.

Filling Medium

The filling medium provides centering, volume, index of refraction, defines anterior and posterior radii of curvature, and provides a natural dynamic response to accommodative changes in the suspensory ligament. It is therefore important that the filling medium resist gravitationally induced asymmetry, yet provide for symmetrical compliance.

The filling medium is preferably bi-phasic, comprised mostly of water and a small structure component of polymeric chains. The water comprises between 50 and 95% of the total volume, with the remainder occupied by polymeric solids. There are a variety of structured organic and inorganic prepolymers suitable for the present invention. It is preferred that the filling medium be delivered to the implanted capsular interface as a prepolymer which then polymerizes in situ. Poly-urea-urethanes are ideal for this purpose, and a variety of prepolymers are commercially available. The advantage of the polymeric systems is that they do not degrade readily in the body. There are a variety of UV curing polymer available that are also suitable.

Preferably, the structural geometry of the filling medium possess the following features: 1) the prepolymer is able to bond to anterior and posterior inner surfaces of the capsular interface and 2) that some degree of cross linking occurs such that linear chains disposed between anterior and posterior inner surfaces of the capsular interface are linked laterally. This later point may be significant in the context of an IOL formed in situ. Thus, a patient is typically positioned horizontally on their back for surgery, the natural lens is removed and an IOL is implanted. In the case of a traditional, preformed implant, the implant is inserted, the incision is made water tight, and the patient is permitted to ambulate. With an in-situ formed implant, however, if the implant is not sufficiently cured or is not polymeric, when the patient ambulates the change in gravitational force from anterior-posterior while the patient is horizontal to cephalad-caudad while the patient ambulates, may adversely affect the shape of the implant and, further, the accommodative function of the lens. Not all the polymeric chains must be bonded to both anterior and posterior surfaces, and not all of the polymeric chains need to be cross linked laterally. Thus a mixture of di-functional and tri-functional or greater prepolymers are useful. The effect of these polymeric links is to prevent asymmetric sagging of the capsular interface. In particular, for the polymer to dilate in the anterior-posterior plane the polymer must contract in the equatorial (cranial-caudal) plane.

Enhanced anterior-posterior dilation and consequently increased gain can be achieved without introducing asymmetry due to gravity by providing for anterior-posterior links primarily through anterior bond chains and separately posterior bonded chains linked through lateral bonds. Furthermore, a minority of free chains may be interposed to provide for greater mobility requiring less accommodative force to achieve a desired change in radial curvature of the anterior and posterior sections of the capsular interface. More complex geometries can be achieved by varying the ratio of anteriorly bonded chains to posteriorly bonded chains so that the radius of curvature on the anterior side is greater or less than the radius of curvature on the posterior side. In this way an IOL implant can be constructed that maintains a variety of ellipsoidal geometries as well as compound geometries which are more ellipsoidal on the periphery and more spherical at the center. Accordingly, the preferred prepolymer mixtures of the present invention when filled into a capsular interface possess an internal structure that tends to stabilize the shape of the IOL in an ellipse with an aspect ratio<0.6, and more preferably between 0.45 and 0.6.

Biocompatibility

In addition to selecting relatively inert and stable compounds for implantation, it is desirable the surface of the IOL follows without relative motion changes in shape of the natural capsule. Abrasion between an implant and the natural capsule can cause fibrosis and opacity, which when in the field of view obscures vision.

Additionally, the exterior surface of the IOL, especially the posterior surface, may be coated with a lubricous material designed to mitigate irritation of the capsule and reduce posterior capsular opacification typically associated with IOLs. Suitable lubricious materials are silicone oils, placed peri-operative behind the implant or bonded directly to the implant. There are a variety of techniques known in the art for bonding lubricous surfaces, such as silicone oil, to an elastomeric substrate. Preferably, the area of lubricity is located away from the area of localization of the present invention.

Ultra-Violet Protection

It is standard practice to add chromophores to IOLs to reduce the intensity of ultra-violet light transmission through an IOL. All the embodiments of the present invention can have chromophores added to the filling medium prior to solidification within the capsular interface. Compatible chromophores include benzotri-azole benophenones with an absorption spectrum extending to wavelengths as long as 400 nm.

The methods and systems of the present invention, as described above and shown in the drawings, provide for IOL devices and methods with superior properties including improved functional approximation of a healthy lens. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A physiologically adaptive intra-capsular optic comprising:
   an injectable filling medium; and
   a capsular interface configured and dimensioned to be received within the natural eye capsule, and to be filled with the injectable filling medium, wherein the capsular interface filled with the filling medium defines a first optical power, wherein the capsular interface filled with the filling medium is an elastic accommodative lens so as to respond to action of the ciliary muscles and adjust to an altered shape,
   wherein the capsular interface and the filling medium are configured to define a second optical power of the elastic accommodative lens in the altered shape after responding to action of the ciliary muscles,
   wherein the first and second optical powers are predetermined by at least the shape and refractive index of the capsular interface, and the refractive index of the injectable filling medium, such that the first and second optical powers vary depending on the shape and refractive index of the capsular interface, and the refractive index of the injectable filling medium,
wherein the filling medium comprises a three-dimensional polymeric network to provide internal structure to the capsular interface,
wherein the three-dimensional polymeric network comprises an internal strip comprising two or more segments joined by a preferential bend point; and
wherein the filling medium is comprised of a block polymer containing at least one silicon block.

2. An intra-capsular optic as recited in claim 1, wherein the capsular interface is at least one of rolled or folded and inserted through a small incision in the eye and filled in situ by injecting the filling medium into said capsular interface.

3. An intra-capsular optic as recited in claim 2, wherein the injectable filling medium changes from a liquid state to a solid state.

4. An intra-capsular optic as recited in claim 3, wherein the said solid state is structured and biphasic comprised of between 50 and 95% liquid and a solid distributed state.

5. An intra-capsular optic as recited in claim 4, wherein anterior and posterior inner walls of said capsular interface are bonded at least partially to the bi-phasic filling medium.

6. An intra-capsular optic as recited in claim 1, wherein the capsular interface further comprises a deployment means such that when the capsular interface is filled with the filling medium, the conduit for delivery is sealed, and a delivery means is detached from said capsular interface, and wherein the deployment means includes a catheter.

7. An intra-capsular optic as recited in claim 6, wherein the interior volume of the capsular interface is fluidically connected to said catheter.

8. An intra-capsular optic as recited in claim 6, wherein the capsular interface includes a valve for sealing the conduit for delivery.

9. An intra-capsular optic as recited in claim 4, wherein said liquid fraction is selected to obtain a desired optical power.

10. An intra-capsular optic as recited in claim 1, wherein at least one of the filling medium or the material of the capsular interface is selected to obtain a desired optical power.

11. An intra-capsular optic as recited in claim 1, wherein the capsular interface is filled to obtain an aspect ratio less than 0.6.

12. An intra-capsular optic as recited in claim 11, wherein the capsular interface when filled has dimension of approximately 4 mm anteroposteriorly and 9 mm equatorially.

13. An intra-capsular optic as recited in claim 1, wherein the capsular interface is scalloped on the equatorial periphery.

14. An intra-capsular optic as recited in claim 1, wherein the capsular interface is coated with a medication.

15. An intra-capsular optic as recited in claim 1, wherein at least part of the filling medium contains a medication and the capsular interface is selectively permeable to the medication.

16. An intra-capsular optic as recited in claim 1, wherein the shape of the optic is defined at least in part by the capsular interface, and the shape defined by the capsular interface at least in part defines the optical power of the optic.

17. An intra-capsular optic as recited in claim 1, wherein the capsular interface includes multiple layers which in combination at least in part define the optical power of the optic.

18. An intra-capsular optic as recited in claim 1, wherein a portion of the capsular interface within the field of view is less elastic than a portion of the capsular interface outside of the field of view.

19. An intra-capsular optic as recited in claim 1, wherein the injectable filling medium is an in-situ polymerizing filling medium.

20. An intra-capsular optic as recited in claim 1, wherein the shape of the optic is defined by the capsular interface, and the shape defined by the capsular interface at least in part defines the optical power of the optic such that the optic has a predetermined optical power.

21. An intra-capsular optic as recited in claim 1, wherein the first optical power provides for corrected distance vision.

22. An intra-capsular optic as recited in claim 1, wherein the first optical power provides for corrected near vision.

23. An intra-capsular optic as recited in claim 1, wherein the exterior surface of the capsular interface is coated with a lubricous material.

24. An intra-capsular optic as recited in claim 1, wherein the exterior surface of the capsular interface is coated with a material designed to mitigate irritation of the capsule.

25. An intra-capsular optic as recited in claim 1, wherein the exterior surface of the capsular interface is coated with a material designed to reduce posterior opacification.

26. An intra-capsular optic as recited in claim 1, wherein the filling medium includes a material designed to reduce the intensity of ultra-violet light transmission.

27. An intra-capsular optic as recited in claim 1, wherein the filling medium is a hydrogel.

28. An intra-capsular optic as recited in claim 1, wherein the filling medium is a nonstructural medium such as saline, glycerin, or hyaluronic acid.

29. An intra-capsular optic as recited in claim 6, wherein the capsular interface includes a valve for sealing the conduit for delivery.

30. A physiologically adaptive intra-capsular optic comprising:
an injectable filling medium; and
a capsular interface configured and dimensioned to be received within the natural eye capsule, and to be filled with the injectable filling medium, wherein the capsular interface filled with the filling medium defines a first optical power, wherein the capsular interface filled with the filling medium is an elastic accommodative lens so as to respond to action of the ciliary muscles and adjust to an altered shape,
wherein the capsular interface and the filling medium are configured to define a second optical power of the elastic accommodative lens in the altered shape after responding to action of the ciliary muscles,
wherein the first and second optical powers are predetermined by at least the shape and refractive index of the capsular interface, and the refractive index of the injectable filling medium, such that the first and second optical powers vary depending on the shape and refractive index of the capsular interface, and the refractive index of the injectable filling medium,
wherein the three-dimensional polymeric network comprises an internal strip comprising two or more segments joined by a preferential bend point, and
wherein the filling medium is a silico-urethane prepolymer comprised of a block polymer containing at least one silicon containing block and at least one ethylene oxide containing block.

31. An intra-capsular optic as recited in claim 30, wherein the capsular interface further comprises a deployment means such that when the capsular interface is filled with the filling medium, the conduit for delivery is sealed, and a delivery means is detached from said capsular interface.

32. An intra-capsular optic as recited in claim 31, wherein the deployment means includes a catheter, and the interior volume of the capsular interface is fluidically connected to said catheter.

33. An intra-capsular optic as recited in claim 31, wherein the deployment means includes an implantation device.

34. An intra-capsular optic as recited in claim 29, wherein the implantation device is suitable for delivering the filling medium in a fluid state comprising a sealing mechanism to prevent extrusion of the solidified filling medium.

35. An intra-capsular optic as recited in claim 29, wherein the implantation device, which when deployed in filling the capsular interface, causes the capsular interface to separate from the implantation device in a way that minimizes the likelihood of capsular disruption.

* * * * *